United States Patent [19]

Wright et al.

[11] Patent Number: 4,781,201

[45] Date of Patent: Nov. 1, 1988

[54] CARDIOVASCULAR ARTIFACT FILTER

[75] Inventors: John C. Wright; Harry M. Triebel, both of New Haven, Conn.

[73] Assignee: American Home Products Corporation (Del.), New York, N.Y.

[21] Appl. No.: 887,318

[22] Filed: Jul. 22, 1986

Related U.S. Application Data

[63] Continuation of Ser. No. 686,575, Dec. 27, 1984, abandoned.

[51] Int. Cl.⁴ .............................................. A61B 5/08
[52] U.S. Cl. ...................................... 128/671; 128/696; 128/706; 128/708; 128/709; 128/723; 364/413.03; 364/724.19
[58] Field of Search ............... 128/696, 706, 708, 716, 128/721, 723, 670, 671; 382/6, 54; 333/16 S; 364/415, 724

[56] References Cited

U.S. PATENT DOCUMENTS

| | | | |
|---|---|---|---|
| 3,587,562 | 6/1971 | Williams | 128/696 |
| 3,740,591 | 6/1973 | Butler et al. | 333/165 |
| 4,140,975 | 2/1979 | Cochran et al. | 333/165 |
| 4,201,977 | 5/1980 | Shimiza | 382/54 |
| 4,223,682 | 9/1980 | Sherman | 128/672 |
| 4,379,460 | 4/1983 | Judell | 128/723 |
| 4,422,458 | 12/1983 | Kravath | 128/696 |
| 4,494,551 | 1/1985 | Little, III et al. | 128/696 |
| 4,537,196 | 8/1985 | Phillips et al. | 128/630 |
| 4,582,068 | 4/1986 | Phillipps et al. | 128/716 |

FOREIGN PATENT DOCUMENTS 2017312 10/1979 United Kingdom ............... 128/696

OTHER PUBLICATIONS

Design of Microcomputer-based Medical Instrumentation by Tompkins et al., published in 1981 by Prentice-Hall, Inc., Pertinent p. 106, lines 21-29.

Primary Examiner—Lee S. Cohen
Assistant Examiner—David Shay
Attorney, Agent, or Firm—Egon E. Berg

[57] ABSTRACT

For suppressing cardiovascular artifact from a respiration signal derived from a patient's transthoracic impedance, an adaptive filtering device determines the patient's heart rate, converts the respiration signal from an analog to digital representation at a rate proportional to the heart rate, and then filters the digital respiration signal such that that portion of the respiration signal having a frequency content at or above the heart rate is most greatly attenuated.

5 Claims, 4 Drawing Sheets

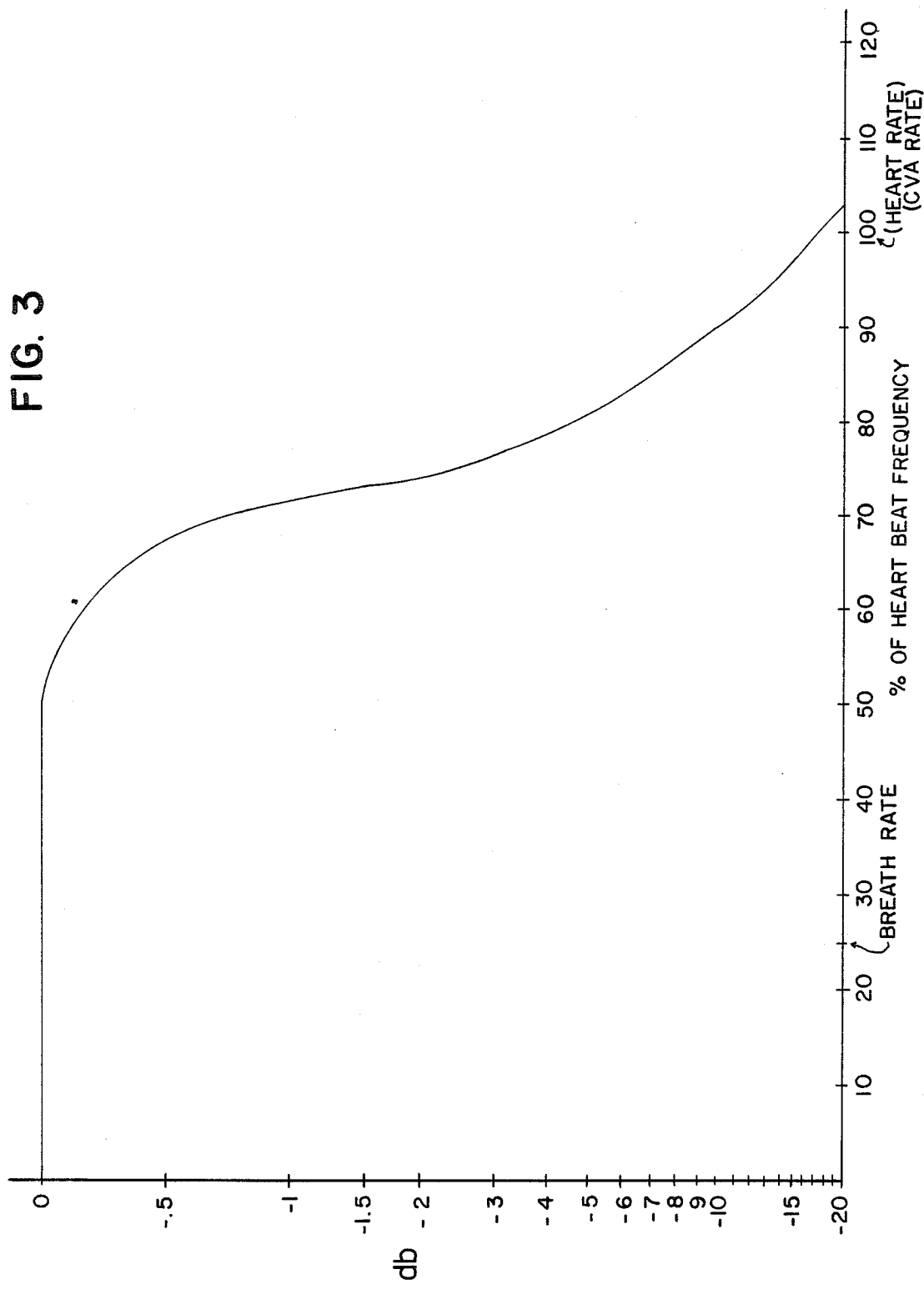

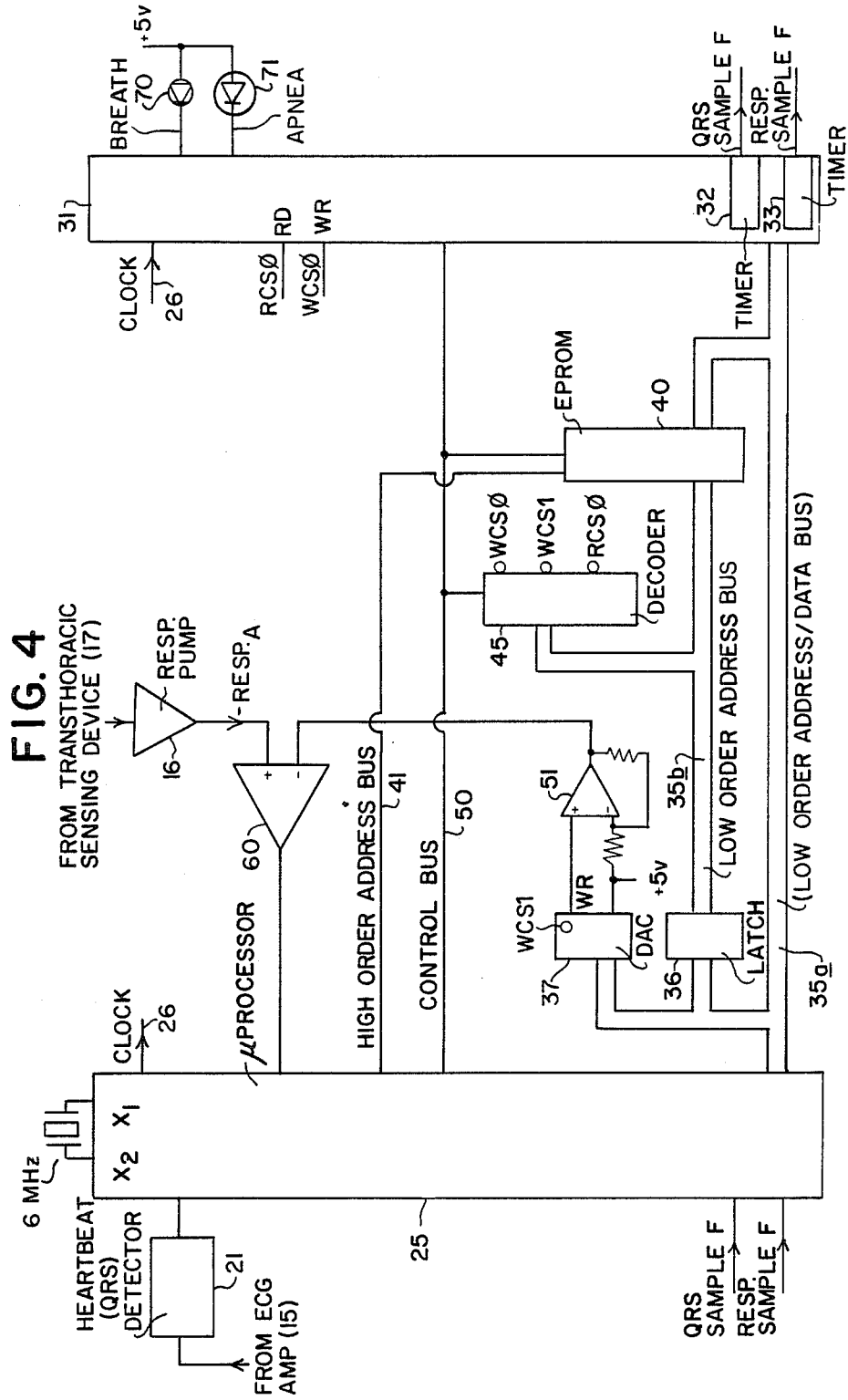

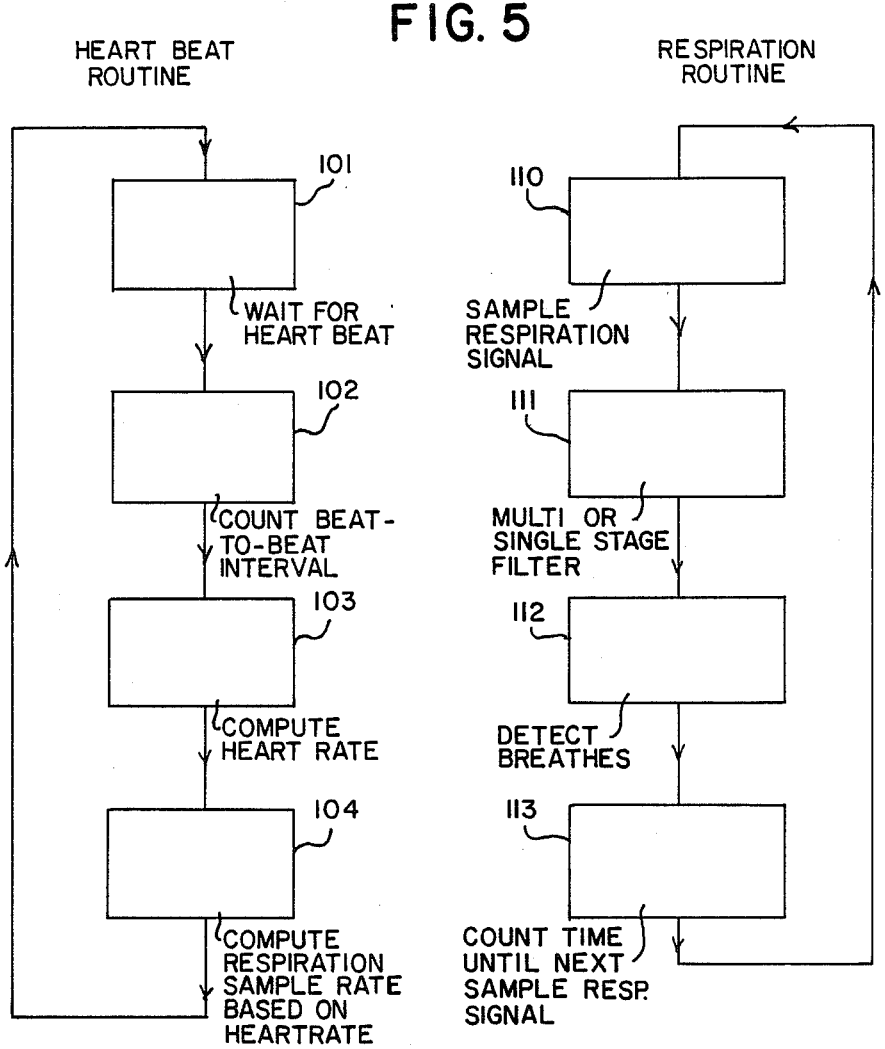

CARDIOVASCULAR ARTIFACT FILTER

This is a continuation of application Ser. No. 686,575, filed Dec. 27, 1984, now abandoned.

BACKGROUND OF THE INVENTION

1. Field of the Invention

The present invention relates to impedance pneumography and more particularly is directed toward suppressing cardiovascular artifact within a respiration signal obtained through impedance pneumography.

2. Description of the Prior Art

A respiration signal is a measure of a patient's transthoracic impedance, that is, the impedance across a patient's chest which varies primarily due to the expansion and contraction of the lungs during breathing. Heart and blood motion also cause a change in the chest size, and thus, a change in the respiration signal. Thus, the respiration signal really comprises both a breath component and a component due to heart and blood motion referred to hereinafter as to cardiovascular artifact.

Therefore, in determining a condition of apnea in the patient, that is, whether the patient has ceased breathing it is highly desirable to identify and suppress those components in the respiration signal which are due to heart and blood motion so that the time duration between breaths can be measured. Otherwise, cardiovascular artifacts can be mistakenly interpreted as breath events when, in fact, a condition of apnea exists. On the other hand, if the breath component of the respiration signal is suppressed in order to remove cardiovascular artifacts, the filtered respiration signal may be incorrectly interpreted as representing a condition of apnea.

One general solution for suppressing cardiovascular artifacts from the respiration signal is based on the fact that cardiovascular artifacts normally have frequencies near or above the heart rate. Accordingly, as long as the heart rate is greater than the breath rate, the cardiovascular artifact within the respiration signal can be greatly reduced, that is, suppressed by removing those components of the respiration signal having frequencies at or above the heart rate. The resulting filtered respiration signal will contain basically only the breath component. The removal, that is, the filtering of such selected frequencies based on another time variant parameter such as heart rate is commonly referred to as adaptive filtering.

Prior art adaptive filters for suppressing cardiovascular artifacts from a respiration signal, commonly referred to as cardiovascular artifact (CVA) filters, typically implement a scheme in which a signal sample is added to previous samples which have been multiplied by one of a number of different coefficients. The choice of coefficients which vary in value based on the heart rate determines the filter's characteristics.

In today's computer era, CVA filtering schemes are typically implemented by employing one or more microprocessors. These microprocessors besides processing the CVA filtering scheme are used for undertaking a number of other tasks which are unrelated to the filtering scheme. In light of these other tasks, the processing time required to execute the above adaptive filtering scheme has taken on added importance. In this regard, the above CVA filtering scheme is considered less than optimal since the frequent change of coefficients requires a relatively large amount of execution time. Additionally such an adaptive filtering scheme requires an undesirable amount of hardware, that is, memory for storing these coefficients. The additional execution time and memory required, of course, result in a more expensive microprocessor system.

OBJECTS AND SUMMARY OF THE INVENTION

Accordingly, it is an object of the present invention to provide a filter for suppressing cardiovascular artifacts from a respiration signal which avoids the drawbacks of the prior art.

More specifically, it is an object of the present invention to provide a new and improved filter for suppressing cardiovascular artifacts from a respiration signal employing a filtering scheme which requires less processing time.

It is another object of the present invention to provide a filter for suppressing cardiovascular artifacts from a respiration signal which requires less microprocessor hardware.

In accordance with an aspect of this invention, a filtering device having a cutoff frequency for suppressing cardiovascular artifacts derived from a patient comprises heart beat detecting means for detecting the heart beats of the patient; processing means for determining the heart rate of the patient in response to the detected heart beats; and filtering means for attenuating a portion of the frequency spectrum of the respiration signal based on the rate at which the filtering means samples the respiration signal wherein the sampling rate is proportional to the heart rate and whereby the cutoff frequency varies in proportion to the sampling rate.

It is a feature of the present invention that the hear beat detecting means comprises a QRS detecting means for detecting the QRS complex of each heart beat waveform produced by the patient. It is another feature of the present invention to provide conversion means for converting from an analog to a digital representation of the respiration signal at a converting rate proportional to the heart rate and wherein the filtering means samples the digital representation of the respiration signal. Other features of the present invention provide two timers one of which clocks the elapsed time between hear beats of the patient and the other of which controls the rate at which the conversion means converts from the analog to a digital representation of the respiration signal. It is still another feature of the present invention to provide a successive approximating analog-to-digital converter as the conversion means.

In accordance with another aspect of the present invention, a method for suppressing cardiovascular artifact from a respiration signal derived from a patient comprises detecting the heart beats of the patient, determining the heart rate of the patient in response to the detected heart beats, and attenuating a portion of the frequency spectrum of the respiration signal wherein each component of the respiration signal within this portion is attenuated in accordance with the ratio of the component's frequency relative to the heart rate.

In regard to this latter aspect of the present invention, features of the invention provide that the method further comprises converting from analog to digital values of the respiration signal at a conversion rate proportional to the heart rate. Another feature of this latter aspect of the present invention provides that the rate at which attenuated respiration signal values are computed is proportional to the converting rate.

The above and other objects, features, and advantages of this invention will become apparent from the following detailed description which is to be read in conjunction with the accompanying drawings.

BRIEF DESCRIPTION OF THE DRAWINGS

FIG. 3 is a Bode plot showing the frequency response of a preferred embodiment of the present invention;

FIG. 4 is a detailed block diagram, partially in schematic form, of a filter in accordance with a preferred embodiment of the present invention; and FIG. 5 illustrates flow charts of a heart beat routine and of a respiration routine in accordance with the embodiment shown in FIG. 3.

DETAILED DESCRIPTION OF A PREFERRED EMBODIMENT

Figure 1:
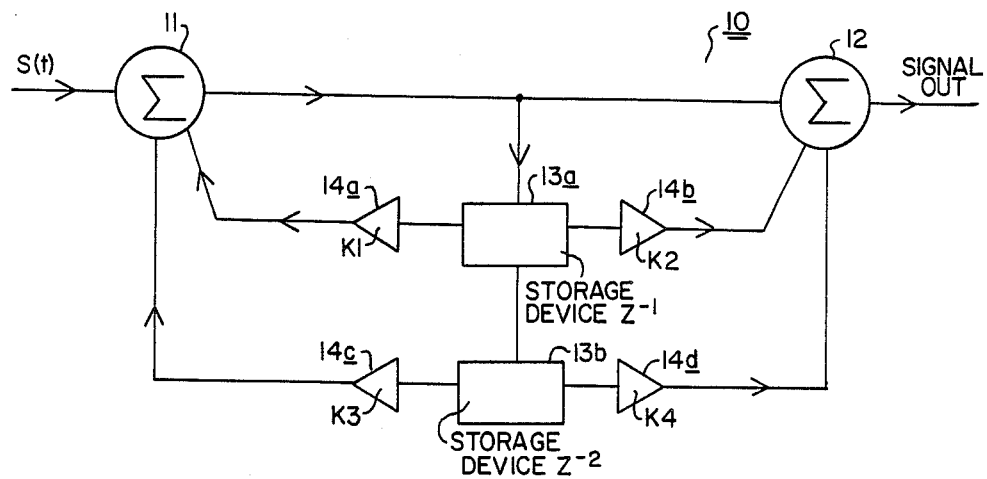
FIG. 1 is a schematic drawing, partially in block form, illustrating a low pass filter.

Shown in FIG. 1 is a single stage, two pole filter 10 for use in suppressing cardiovascular artifacts within a respiration signal. The respiration signal input is derived from a patient based on the patient's transthoracic impedance. Filter 10 comprises a summer 11 connected to both a summer 12 and a storage device 13a commonly referred to as $Z^{-N}$. Two amplifiers 14a and 14b, which multiply their respective input signals by factors $K_1$ and $K_2$, are connected at their respective input terminals to output terminals of storage device 13a. The output terminals of amplifiers 14a and 14b are connected to input terminals of summers 11 and 12, respectively. An additional storage device ($Z^{-N}$) 13b is also connected to an output terminal of storage device 13a. Two additional amplifiers 14c and 14d, which multiply their respective input signals by factors $K_3$ and $K_4$, are connected at their input terminals to output terminals of storage device 13b. The output terminals of amplifiers 14c and 14d are connected to two additional input terminals of summers 11 and 12, respectively. Operation of filter 10 can be most simply described according to the following equation:

Signal Out
$$(t) = S_{(t)} + (K_1 + K_2)Z^{-1}{}_{(t-1)} + (K_3 + K_4)Z^{-2}{}_{(t-1)} \quad \text{(eq. 1)}$$

where:

$S_{(t)}$ is the respiration sample at time t
$K_1$ is the multiplying factor of amplifier 14a
$K_2$ is the multiplying factor of amplifier 14b
$K_3$ is the multiplying factor of amplifier 14c
$K_4$ is the multiplying factor of amplifier 14d $$Z^{-1}{}_{(t)} = S_{(t)} + K_1 Z^{-1}{}_{(t-1)} + K_3 Z^{-2}{}_{(t-1)}$$

$$Z^{-2}{}_{(t)} = Z^{-1}{}_{(t-1)}$$

Filter 10 has a filtering characteristic dependent upon the choice of values selected for factors $K_1$, $K_2$, $K_3$ and $K_4$ and the rate at which the respiration samples are clocked through filter 10. By dynamically varying the values of $K_1$, $K_2$, $K_3$ and $K_4$ based on the heart rate, filter 10 becomes an adaptive filter typically used in the prior art for suppressing cardiovascular artifacts and thereby for providing a respiration signal containing only the breath component. The respiration signal is being sampled by filter 10 at a constant rate. The above adaptive filtering scheme, however, has two important drawbacks. More specifically, filter 10 if implemented, in part, by employing a microprocessor requires less than an optimal amount of execution time due to the frequent changes of coefficients ($K_1$-$K_4$) required. Additionally, such an adaptive filter requires far too much microprocessor hardware due to the memory necessary to store all of these coefficients.

The present invention avoids such prior art drawbacks by employing an adaptive filtering scheme which is based on the well known premise that the artifact present in the respiration signal is comprised of frequencies equal to or at multiples of the heart rate. More specifically, however, rather than varying coefficients $K_1$-$K_4$ while maintaining a constant rate at which the rspiration signal is being sampled as in the prior art, the present invention advantageously varies the rate at which the respiration signal is being sampled while maintaining coefficients $K_1$-$K_4$ constant. In other words, the filtering characteristics of the present invention are varied by changing the rate at which data is clocked therethrough.

Figure 2:
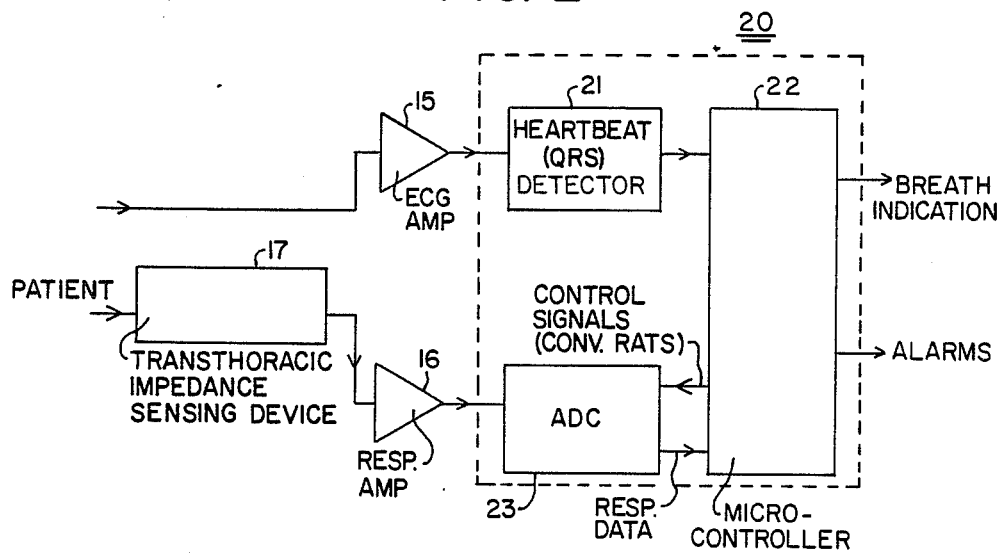
FIG. 2 is a block diagram of the present invention.

Referring now to the present invention as shown in FIG. 2, an electrocardiogram (ECG) signal obtained from a patient is fed into an ECG amplifier 15 and the respiration signal, which includes cardiovascular artifact, is supplied to respiration amplifier 16 by a transthoracic sensing device 17. Amplifier 15 has a gain of 1000 millivolts (mv) per 1 mv of ECG signal and a bandwidth of 1 to 100 hertz (Hz). Amplifier 16 has a gain of 0.4 volts per ohm of transthoracic impedance variation and a bandwidth of 0.2 to 2.5 Hz. Transthoracic impedance sensing devices, such as device 17, are well known in the art of respiration monitoring and are essentially merely a.c. ohmmeters. Filter 20 shown within dashed lines, comprises a heart beat detector 21, a microcontroller 22 and an analog-to-digital converter 23. Heart beat detectors such as detector 21 normally detect the QRS complex of the waveform of the patient and are well known in the field and need not be described further. Detector 21 is connected to the microcontroller 22 and supplies to the latter a signal each time a heart beat is detected. Microcontroller 22, which comprises a microprocessor, an erasable-programmable-read-only-memory (EPROM), a latch, an input/output (I/O) buffer and two timers, processes, that is, determines the heart rate of the patient based on these detected heart beats and supplies control signals to converter 23 so as to control the rate at which the respiration signal is converted from an analog-to-digital representation by converter 23. The respiration data supplied by converter 23 is then filtered by microcontroller 22 to remove the CVA and then processed to determine the time of occurrence of each breath. Based on the breath events, microcontroller 22 triggers an alarm indicating the lack of respiration commonly referred to as apnea and a breath event indicator.

The conversion rate of converter 23, that is, the rate at which the analog signal is being sampled by converter 23 is directly proportional to the heart rate. In the preferred embodiment, the converting rate has been set at ten times the heart rate. As is well known in the art based on the Nyquist (Sampling) theorem, a sampling rate must be at least twice the highest frequency component in order to completely characterize a signal. The minimum value of the sample rate is 5 Hz which is ten times the minimum computed heart rate of 0.5 Hz (30 beats per minute). As previously noted, the respiration signal amplifier 16 limits the respiration signal to those components less than 2.5 Hz. Thus the 5 Hz minimum sample rate is twice the highest respiratory component of 2.5 Hz.

The cutoff frequency of filter 20 is directly proportional to the conversion rate and thus proportional to the heart rate. Consequently, by employing the adaptive filtering scheme of FIG. 2, portions of the respiration signal having a frequency content at or above the heart rate are significantly attenuated while those components of the respiration signal having a frequency content at half or less the heart rate are substantially unattenuated. In other words, the adaptive filtering scheme of the present invention provides a low pass filter. Guidelines for attentuation of the respiration signal will be discussed in greater detail below.

A Bode plot of the CVA filter of the present invention is shown in FIG. 3 wherein the abscissa contains all the frequency components of the respiration signal expressed as a percentage of the patient's heart beat frequency and wherein the ordinate represents the amplitude of each frequency component of the filter output expressed in decibels (db).

The present invention operates as a low pass filter which preferably has a cutoff frequency, that is, a $-3$ db point, equal to approximately 78.4% of the fundamental heart beat frequency. Accordingly, the present invention provides a filtering device for attenuating a portion of the frequency spectrum of the respiration signal such that the cutoff frequency varies in proportion to the heart rate. The filter provides attenuations of approximately 17 db, 10 db, and 1.5 db for those components of the sampled respiration signal's frequency spectrum at 100%, 90% and 75% of the heart rate, respectively. Additionally, the filter provides approximately zero attenuation for those components of the frequency spectrum of the sampled respiration signal at 50% or less of the heart rate.

As now can be readily appreciated, since the respiration rate is normally a small percentage of the heart rate, the present invention substantially suppresses the cardiovascular component relative to the breath component of the respiration. For example, assume for illustrative purposes only that the respiration signal comprises a breath component at a single frequency of 0.25 Hz (15 breaths per minute) and a cardiovascular component at a single frequency of 1 Hz (60 beats per minute). The breath rate represents 25% of the heart beat frequency and the cardiovascular rate is shown only at the fundamental heart beat frequency. Therefore, the breath component will not be attenuated at all whereas the CVA component will be attenuated by approximately 17 db by the present invention.

Referring now to FIG. 4, a preferred embodiment of the present invention is shown in which elements similar to those discussed in connection with FIG. 2 are identified by the same reference numerals. An adaptive filter 20a comprises heart detecting means 21 connected to a microprocessor 25. A 6 MHz system clock for microprocessor 25 is connected to terminals $X_1$ and $X_2$ of the microprocessor. The 6 MHz system clock is divided by microprocessor 25 for providing various clock signals including a clock signal CLOCK of 400 KHz (a 2.5 microsecond period) which is supplied to chip 31 on line 26. Chip 31 comprises a random access memory (RAM), an input/output (I/O) buffer and two timers. Microprocessor 25 is an 80C39, 8 bit microprocessor and may be obtained from a number of manufacturers such as the Intel Corporation. Chip 31 is an NSC810 manufactured by the National Semiconductor Corporation.

An 8 bit low order address/data bus 35a is connected between microprocessor 25 and integrated package 31 and is also connected to a latch 36, a digital-to-analog converter (DAC) 37 and an erasable-programmable-read-only-memory (EPROM) 40. A separate low order address bus 35b is connected between latch 36, a decoder 45 and EPROM 40. A high order 8 bit address bus 41 is connected between EPROM 40 and microprocessor 25. Latch 36 is an 8 bit latch commonly identified within the industry as a 74HC373 which is used to store the addresses of data processed by microprocessor 25. Decoder 45 has eight output terminals three of which are shown as WCS0, WCS1 and RCS0. Terminals WCSO and RCSO are connected to the write and read terminals of chip 31, respectively. Terminal WCS1 is connected to the write terminal (WR) of DAC 37. Decoder 45 is used for selecting among microprocessor 25, latch 36, EPROM 40 and chip 31 by sending control signals on a control bus 50.

Chip 31 and microprocessor 25 are also connected together by line QRS Sample F and by line RESP Sample F. As will be discussed below, these lines are used for determining the elapsed time between heart beats and for triggering/beginning the analog-to-digital conversion of the respiration signal, respectively. Connected to the output of DAC 37 is a current-to-voltage converter 51 which converts the current signal supplied by DAC 37 into an analog voltage. The output of converter 51 is connected to the inverting input of a comparator 60. Supplied to the non-inverting input of comparator 60 is the analog representation of the sampled respiration signal provided by respiration amplifier 16 and identified as $RESP_A$. The output of comparator 60 is supplied to microprocessor 25.

Device 20a operates as follows: Initially microprocessor 25 loads a starting value into timer 32 of integrated package 31 according to instructions stored in EPROM 40, which contains all the programs for operating device 20a. Timer 32, which is a down counter, decrements from this starting value every 2.5 microseconds based on the CLOCK signal received from microprocessor 25 on clock line 26. Once counter 32 decrements to a value of zero, a pulse is sent along line QRS Sample F to microprocessor 25. Thus each pulse sent along line QRS Sample F represents a predetermined elapsed period of time. Microprocessor 25 keeps a running tab of the number of pulses received along line QRS Sample F between heart beats determined by heart beat detector 21. Based on the number of pulses received along QRS Sample F line between heart beats, microprocessor 25 is able to determine the heart beat rate. For example, if each pulse supplied by QRS Sample F line is equal to an elapsed time of 25 milliseconds, then if 40 pulses are received by microprocessor 25 between two heart beats, the heart rate would be 60 beats per minute. Once timer 32 reaches a value of zero it will automatically reload to the starting value set by EPROM 40 and continues to recycle through this counting scheme thereafter. Based on the computed heart rate, microprocessor 25 will be directed by EPROM 40 to load one of over one hundred fifty different starting values in a second timer 33 of chip 31. These starting values are stored in a table within EPROM 40 and correspond to the computed heart rate. Timer 33 is also decremented based on a clock signal derived from CLOCK signal, that is, timer 33 is decremented every 10 microseconds. Once timer 33 reaches a value of zero, a pulse is sent along RESP Sample F line and received by microprocessor 25 which triggers, that is, begins the start of conversion of the analog-to-digital representation of the respiration signal. Higher or lower initial values are used for resetting timer 33 when a slower or faster conversion rate is desired, respectively. As can now be readily appreciated, the rate at which the respiration signal will be sampled and converted from an analog to digital representation is determined based on the heart rate.

In converting the respiration signal from an analog-to-digital form, a successive approximation technique is employed which utilizes microprocessor 25, DAC 37, current-to-voltage converter 51, and comparator 60. This technique is well known in the art and will therefore only be briefly described herein. More specifically, microprocessor 25 will supply a first approximating ten bit signal having a value midway between the highest and lowest signals which can be produced by respiration amplifier 16. The first approximating signal produced by microprocessor 25 is nothing more than an intelligent guess as to the actual value of the respiration signal ($RESP_A$) produced by respiration amplifier 16. DAC 37 will convert this first approximating signal to an equivalent analog current value which is then converted to an equivalent voltage by current-to-voltage converter 51. The analog output from converter 51 is supplied to the inverting input of comparator 60 and compared to the sampled respiration signal ($RESP_A$) supplied by respiration amplifier 16 to the noninverting input of comparator 60. The output signal from comparator 60 is supplied to and used by microprocessor 25 for determining the next, that is, successive approximating signal produced by microprocessor 25. Through this repetitive process, which is repeated ten times, microprocessor 25 "zeros-in" on the digital value of $RESP_A$. The foregoing successive approximation technique can be easily defined in terms of an algorithm by one of ordinary skill in the art and more particularly is defined by a computer program which is used by filtering device 20a and which is found at the end of this detailed description of a preferred embodiment. The computer program also discloses all of the foregoing steps involved in determining the heart rate and the rate at which the respiration signal is sampled for purposes of conversion from an analog to digital representation. As now can be readily appreciated, the ADC 23 of FIG. 2 is comparable to microprocessor 25, DAC 37, converter 51 and comparator 60 of FIG. 4.

Once the digital representation of the sample representation signal has been determined EPROM 40 is notified of the same through latch 36 by requesting the next instruction from EPROM 40 as to what to do with this digital value. Consequently, EPROM 40 will instruct microprocessor 25 to filter this digital sample respiration signal according to the filtering scheme of FIG. 1 and as described by eq. 1 above wherein the values of $K_1$, $K_2$, $K_3$ and $K_4$ are not dynamically varied based on the heart rate as in the prior art but rather are maintained at fixed values while the rate at which the sampled signal is filtered is varied based on the heart rate. Eq. 1 can be readily implemented by one of ordinary skill in the art of computer software using a number of different computer programs. One such computer listing is disclosed below in the computer program.

Microprocessor 25 then uses the filtered sample of the respiration signal, which comprises the unattentuated breath component and substantially suppressed cardiovascular artifacts, in a breath detection algorithm to determine when each breath occurs. This algorithm is also disclosed as part of the computer program.

Light emitting diodes 70 and 71, which are connected to chip 31, are used to alert a user each time a breath and a condition of apnea occurs, respectively. More particularly, the computer program provides a series of instructions for directing diode 70 to light each time a breath occurs and for diode 71 to light when a condition of apnea occurs based on the breath detection algorithm.

Referring now to FIG. 5 the heart beat routine and respiration routine described above and implemented by the computer program are shown in the form of flow charts. The first step (101) in the heart beat routine comprises waiting for the heart beat which is detected by heart beat dectector 21. The beat-to-beat interval between heart beats (step 102) is counted by microprocessor 25. In this regard, the number of pulses supplied along QRS Sample F line between the detected heart beats are counted by microprocessor 25 to determine the elapsed time between the heat beats. In step 103, the heart rate based on the elapsed time between heart beats is computed. Finally, step 104 computes the rate, at which the respiration signal should be sampled based as the heart rate. In filtering device 20a this computation is performed by picking a starting value for timer 33 based on the computed heart rate. Once step 104 has been completed, the heart beat routine returns to step 101.

The respiration routine begins with step 110 which samples the respiration signal. In filtering device 20a step 110 is performed by converting the respiration signal from an analog to digital representation. The next step 111 of the respiration routine is to filter the digital respiration signal using either a single or multi stage filter. The number of stages may be varied in order to achieve the filtering characteristics desired. In the present invention, the filtering scheme comprises four cascaded single stage, two pole filters one of which is shown in FIG. 1 and is implemented according to the computer program. The filtered respiration signal is then used by microprocessor 24 to detect each breath event as identified by step 112. A number of different algorithms including, but not limited to, the algorithm in the computer program can be used for detecting each breath. The final step 113 of the respiration routine counts the time until the next respiration signal is sampled. In the present invention, this counting is done by timer 33. Normally, microprocessor 25 performs the respiration routine at a rate proportional to the last computed heart rate. Periodically, the respiration routine is interrupted and the heart beat routine is performed after which the respiration routine resumes.

As can now be readily appreciated, the present invention provides a CVA filter which effectively suppresses the cardiovascular artifacts within the respiration signal and thereby provides a respiration signal which includes basically only the breath component. Furthermore, as compared to prior art CVA filters, the present invention does not require as much execution time and therefore need not be as sophisticated or as costly as microprocessors presently used for CVA filtering purposes.

Having specifically described an illustrative embodiment of the invention with reference to the accompanying drawings, it is to be understood that the invention is not limited to this precise embodiment and that various changes and modifications may be effected by one skilled in the art without departing from the scope and spirit of the invention as defined by the appended claims. For example, the present invention need not be limited to employing analog to digital converters and may instead directly filter the analog representation of the respiration signal at a sampling rate proportional to the heart rate.

```
;
;*****************************************************
;*      TITLE:    HEART RATE / APNEA MONITOR PROGRAM  *
;*                                                    *
;*            (C) COROMETRICS MEDICAL SYSTEMS, INC.   *
;*      UNPUBLISHED AS OF 12/26/84; INTENDED TO BE PUBLISHED *
;*                  IN 1985. ALL RIGHTS RESERVED.     *
;*****************************************************
;
           NAME    START
;
;************************
;* VARIABLE DEFINITION *
;************************
;
HRATE    EQU      020H
STATUS   EQU      024H
TSTAT    EQU      025H
BBINT    EQU      02DH
BREATH   EQU      02EH
DECAY    EQU      02FH
BRLED    EQU      031H
HRDA     EQU      034H
DADATA   EQU      038H
DELTA    EQU      03AH
NEWCVA   EQU      03CH
RSPSAM   EQU      040H
SAMPLE   EQU      043H
SILCNT   EQU      045H
UPSTAT   EQU      04AH
MINWAV   EQU      05DH
FOURTH   EQU      070H
PAUTO    EQU      072H
PTHRES   EQU      074H
NTHRES   EQU      076H
PORTA    EQU      0C0H
PORTB    EQU      0C1H
DDRA     EQU      0C4H
LSBT1    EQU      0D2H
START1   EQU      0D7H
CRTO     EQU      0D8H
;
;***************************
;* DECLARE ROUTINE NAMES *
;***************************
;
           GLOBAL    INT
           GLOBAL    SAMINT
           GLOBAL    FILTER
           GLOBAL    FILRET
           GLOBAL    COMP2
           GLOBAL    MULT
           GLOBAL    SHIFT
           GLOBAL    ADJUST
           GLOBAL    DECTHS
           GLOBAL    FIXTHS
           GLOBAL    DIVIDE
           GLOBAL    MOVTWO
```

```
        GLOBAL    FDELTA
        GLOBAL    OUTDA
        GLOBAL    SAVEHR
        GLOBAL    FSHLED
        GLOBAL    CLRTWO
        GLOBAL    ROTLFT
        GLOBAL    ROTLOP
;
; DECLARATION OF MODULE SPACE ALLOCATION
;
        SECTION   MAIN,ABSOLUTE
;
        ORG       00H
        SEL       RB0                    ;SELECT REGISTER BANK 0
        JMP       START                  ;GOTO TO START-UP PROGRAM
;
; SET-UP INTERRUPT ROUTINE
;
        SEL       RB1                    ;SELECT REGISTER BANK 1
        JMP       INT                    ;GOTO INTERRUPT ROUTINE
;
; PROGRAM NSC810 I/O PORTS A,B,C TIMER 0 AND TIMER 1
;
START   MOV       R0,#DDRA               ;POINT TO PORT A DATA DIRECTION REG
        MOV       A,#11111000B           ;SET UP I/O CONFIGURATION BITS
        MOVX      @R0,A                  ;SET UP DIRECTION FOR PORT A
        INC       R0                     ;POINT TO PORT B DATA DIRECTION REG
        CLR       A                      ;SET UP I/O CONFIGURATION BITS
        MOVX      @R0,A                  ;SET UP DIRECTION FOR PORT B
        INC       R0                     ;POINT TO PORT C DATA DIRECTION REG
        MOV       A,#00100000B           ;SET UP I/O CONFIGURATION BITS
        MOVX      @R0,A                  ;SET UP DIRECTION FOR PORT C
        CLR       A                      ;CLEAR ACCUM
        INC       R0                     ;POINT TO MODE DEFINITION REGISTER
        MOVX      @R0,A                  ;SET-UP PORTS
        MOV       R0,#PORTA              ;POINT TO PORT A OUTPUT ADDRESS
        MOVX      @R0,A                  ;INITIALIZE PORT A OUTPUT
        MOV       R0,#CRT0               ;POINT TO COMMAND REG FOR T0
        MOV       A,#00001101B           ;SET COMMAND FOR TIMER 0
        MOVX      @R0,A                  ;STORE COMMAND
        INC       R0                     ;POINTTO COMMAND REG FOR T1
        MOV       A,#00000110B           ;SET COMMAND FOR TIMER 1
        MOVX      @R0,A                  ;STORE COMMAND
;
; TEST EACH BYTE OF RAM (01H-7FH) AND THEN INITIALIZE TO 0
;
        CPL       F0                     ;COMPLEMENT FLAG 0 - SET TO 1
        MOV       R0,#07FH               ;SET R0 = LAST LOCATION OF MEMORY
        MOV       A,R0                   ;SET ACCUM = R0 ADDRESS
RAMTST  MOV       @R0,A                  ;STORE ACCUM INTO R0 ADDRESS
        MOV       A,@R0                  ;RECALL BYTE FROM R0 ADDRESS
        CPL       A                      ;COMPLEMENT VALUE - MAKE IT MINUS
        INC       A                      ;ADD 1 TO IT
        ADD       A,R0                   ;ADD TO IT R0 ADDRESS
        JZ        RAMOK                  ;IF BYTE WRITTEN = BYTE READ ? JUMP
        CLR       F0                     ;ELSE CLEAR F0 - INDICATE ERROR
        CLR       A                      ;CLEAR ACCUM
RAMOK   MOV       @R0,A                  ;SET BYTE POINTED TO BY R0 = 0
        DEC       R0                     ;DECREMENT R0 ADDRESS POINTER BY 1
        MOV       A,@R0                  ;RECALL CURRENT R0 ADDRESS
        JNZ       RAMTST                 ;IF ADDRESS > 0 ? CONTINUE TO LOOP
        CPL       F0                     ;ADJUST RAM TEST RESULTS 0=PASS,1=FAIL
        JF0       CYCLE                  ;IF RAM FAILED ? JUMP
        MOV       R0,#TSTAT              ;POINT TO TEST STATUS
```

```
                MOV     @R0,#00001000B      ;SET RAM TEST PASSED
;
; FLASH ALL FRONT PANEL LEDS AND BEEP AUDIO ONCE
;
CYCLE   MOV     A,#080H             ;SET ACCUM = 128
        OUTL    P1,A                ;OUTPUT MSB TO LED SEGMENTS
        MOV     R5,#008H            ;SET LED FLASH COUNTER FOR 8
OUTLOP  CALL    FSHLED              ;FLASH NEXT LED
        MOV     R7,#09CH            ;SET OUTTER LOOP COUNTER = 156
INNLOP  DJNZ    R6,INNLOP           ;LOOP IN INNER LOOP
        DJNZ    R7,INNLOP           ;LOOP IN OUTER LOOP
        DJNZ    R5,OUTLOP           ;FLASH ALL 7 LEDS
;
; SET BEAT-to-BEAT HR = 30 BPM, SET LIMITED HR = 30 BPM
;
        MOV     R7,#01EH            ;SET REG 7 = 30 BPM
        CALL    SAVEHR              ;CALL ROUTINE TO INITALIZE HR
;
; INITIALIZE RESP HYSTERESIS WINDOW AND POS AUTO THRES TO MINIMUM VALUE
;
        CALL    DECTHS              ;INITIALIZE THRESHOLDS TO MINIMUM
;
; INITIALIZE RESPIRATION SAMPLE INTERVAL TO BE 5 Hz (HR=30 BPM)
;
        CALL    SAMINT              ;CALL ROUTINE TO GET SAMPLE INTERVAL
;
; SET T1 FOR NEGATIVE PULSE WAVE, FACTOR 1, .002 Sec/TRANSISION
;
        MOV     R0,#LSBT1           ;POINT TO LSB OF TIMER 1
        MOV     A,#064H             ;SET COUNT = 100
        MOVX    @R0,A               ;OUTPUT LSB OF TIMER 1
        INC     R0                  ;POINT TO MSB OF TIMER 1
        CLR     A                   ;100 * 20.0 uSEC = .002 Sec
        MOVX    @R0,A               ;OUTPUT MSB OF TIMER 1
        MOV     R0,#START1          ;POINT TO START TIMER 1
        MOVX    @R0,A               ;WRITE TO MEMORY TO START TIMER 0
;
; START SILENCE COUNTER = 1 SEC (LEADS OFF AUDIO DISABLED FOR 29 SEC)
;
        MOV     R0,#SILCNT+1        ;POINT TO MSB OF SILENCE COUNTER
        MOV     @R0,#001H           ;SET MSB OF SILENCE COUNTER = 1 SEC
;
; MAIN PROGRAM LOOP TO SAMPLE RESPIRATION DATA
;
LOOP    EN      I                   ;ENABLE INTERRUPT
        JNT0    LOOP                ;IF TEST 0 INPUT IS LOW ? LOOP
;
; COMPUTE "NEW" SAMPLE COUNT FROM HEART RATE
;
        CALL    SAMINT              ;CALL ROUTINE TO GET SAMPLE INTERVAL
;
; NEXT, TEST FOR LEADS OFF ?
;
        MOV     R0,#PORTB           ;POINT TO PORT B INPUT
        MOVX    A,@R0               ;INPUT PORT B STATUS
        JB6     SAPPOX              ;IF LEADS ON ? JUMP
        JMP     LOOP                ;ELSE CONTINUE TO LOOP
;
; IF LEADS ON ? GET 10-bit RESP DATA FROM SUCCESIVE APPROXIMATION
;
SAPPOX  CLR     A                   ;CELAR ACCUM
        MOV     R2,A                ;SET LSB OF RESULTS = 0
        MOV     R3,A                ;SET MSB OF RESULTS = 0
```

```
            MOV     R4,A            ;SET UP LSB OUTPUT BIT = 0
            MOV     R5,#80H         ;SET UP MSB OUTPUT BIT = 80H
                                    ;LOOP HERE 10 TIMES (10 BITS)
SAPLOP      MOV     A,R2            ;GET LSB OF RESULTS
            ORL     A,R4            ;"OR IN" LSB OUTPUT BIT
            MOV     R6,A            ;SAVE AS LSB OF TEMP OUTPUT
            MOV     A,R3            ;GET MSB OF RESULTS
            ORL     A,R5            ;"OR IN" MSB OUTPUT BIT
            MOV     R7,A            ;SAVE AS MSB OF TEMP OUTPUT
            MOV     R0,#007H        ;POINT TO REGISTER 7
            CALL    OUTDA           ;OUTPUT TO D/A R7 & R6
            CLR     C               ;CLEAR CARRY
            MOV     A,R5            ;GET MSB OF OUTPUT BIT
            RRC     A               ;ROTATE ONCE RIGHT -> CARRY
            MOV     R5,A            ;SAVE AS NEW MSB OF OUTPUT BIT
            MOV     A,R4            ;GET LSB OF OUTPUT BIT
            RRC     A               ;ROTATE ONCE RIGHT -> CARRY
            MOV     R4,A            ;SAVE AS NEW LSB OF OUTPUT BIT
            JB5     RSPTRD          ;IF THIS IS NOT 11th TIME THROUGH ?
            JNT1    SAPLOP          ;IF INPUT < REF OUTPUT DO NOT SAVE BIT
            MOV     A,R6            ;RECALL CURRENT LSB OUTPUT VALUE
            MOV     R2,A            ;SAVE AS LSB OF RESULTS
            MOV     A,R7            ;RECALL CURRENT MSB OUTPUT VALUE
            MOV     R3,A            ;SAVE AS MSB OF RESULTS
            JMP     SAPLOP          ;LOOP 10 TIMES
;
; SAVE 8 MSB OF RESPIRATION INPUT SAMPLE FOR POSSIBLE TREND STORAGE
;
RSPTRD      MOV     R0,#RSPSAM      ;POINT TO RESPIRATION SAMPLE
            MOV     A,R3            ;RECALL 8 MSB OF RESP INPUT
            MOV     @R0,A           ;SAVE AS 8 MSB OF RESP SAMPLE
;
; OUTPUT CURRENT RESPIRATION BASELINE RECOVERY STATUS
;
            JZ      SETRBR          ;IF INPUT = -FS ? JUMP
            CPL     A               ;COMPLEMENT INPUT
            JNZ     GETSAM          ;IF INPUT NOT = +FS ? JUMP
SETRBR      INC     R0              ;POINT TO RESP BASELINE RESET COUNTER
            MOV     @R0,#09CH       ;ELSE SET RBR COUNT = 100 mSec
;
; IMPLEMENT 4 STAGE DIGITAL FILTER
;
GETSAM      JMP     FILTER          ;CALL DIGITAL FILTER ROUTINE
;
; FIND 1/4 OF THE FILTERED RESPIRATION DATA (RANGE OF 0-255)
;
FILRET      MOV     R7,#02          ;SET LOOP COUNTER = 2
            CALL    SHIFT           ;CALL ROUTINE TO SHIFT R2,R3
            MOV     R0,#FOURTH      ;POINT TO 1/4 DATA STORAGE
            MOV     @R0,A           ;SAVE 1/4 RESP DATA
;
; SEE IF 1/4 RESPIRATION DATA < LATEST MINIMUM WAVEFORM VALUE
;
            MOV     R1,#MINWAV      ;POINT TO MINIMUM WAVE VALUE
            CPL     A               ;COMPLEMENT 1/4 RESP DATA
            INC     A               ;AND ADD 1 TO IT
            MOV     R2,A            ;SAVE - 1/4 RESP DATA FOR LATTER
            ADD     A,@R1           ;ADD MINIMUM WAVE VALUE TO IT
            JNC     MAXTST          ;IF 1/4 DATA > MINIMUM WAVE ? JUMP
            MOV     A,@R0           ;RECALL 1/4 RESP DATA
            MOV     @R1,A           ;SAVE 1/4 AS MINIMUM WAVE VALUE
;
; SEE IF 1/4 RESPIRATION DATA > LATEST MAXIMUM WAVEFORM VALUE
```

```
;
MAXTST  INC     R1                      ;POINT TO MAXIMUM WAVE VALUE
        MOV     A,R2                    ;RECALL - 1/4 RESP DATA
        ADD     A,@R1                   ;ADD MAXIMUM WAVE VALUE TO IT
        JC      TSTDEC                  ;IF 1/4 DATA < MAXIMUM WAVE ? JUMP
        MOV     A,@R0                   ;RECALL 1/4 RESP DATA
        MOV     @R1,A                   ;SAVE 1/4 AS MAXIMUM WAVE VALUE
;
; TEST TO SEE WHETHER TO DECAY HYSTERESIS WINDOW ?
;
TSTDEC  MOV     R0,#DECAY               ;POINT TO CURRENT DECAY TIMER
        MOV     A,@R0                   ;GET CURRENT DECAY TIMER
        ADD     A,#0E7H                 ;ADD -25 TO TIMER
        JNC     POSTST                  ;IF TIMER < 25 ? JUMP
        MOV     @R0,A                   ;SAVE DIFFERENCE AS DECAY TIMER
        CALL    DECTHS                  ;CALL ROUTINE TO DECAY THRESHOLDS
;
; COMPARE 1/4 RESPIRATION DATA WITH THE POSITIVE AUTO THRESHOLD ?
;
POSTST  MOV     R1,#FOURTH              ;POINT TO 1/4 RESP DATA
        MOV     R0,#PAUTO               ;POINT TO POS AUTO THRESHOLD
        MOV     A,@R0                   ;GET POS AUTO THRESHOLD
        CPL     A                       ;COMPLEMENT IT
        INC     A                       ;AND ADD 1 TO IT
        ADD     A,@R1                   ;ADD 1/4 RESP DATA TO IT
        JNC     NEGTST                  ;IF 1/4 DATA < POS THRESHOLD ? JUMP
;
; POS AUTO THRESHOLD = 1/4 DATA
; NEG AUTO THRESHOLD = NEG AUTO THRESHOLD + "NEW" DIFFERENCE
;
        MOV     R2,A                    ;SAVE DIFFERENCE OF 1/4 DATA - POS AUTO
        MOV     A,@R1                   ;RECALL 1/4 RESP DATA
        MOV     @R0,A                   ;SAVE AS "NEW" POS AUTO THRESHOLD
        INC     R0                      ;POINT TO NEG AUTO THRESHOLD
        MOV     A,@R0                   ;GET NEG AUTO THRESHOLD
        ADD     A,R2                    ;ADD DIFFERENCE OF 1/4 DATA - POS AUTO
        MOV     @R0,A                   ;SAVE SUM AS "NEW" NEG AUTO THRESHOLD
;
; IF 1ST TIME SINCE GOING NEGATIVE ? THEN INCREASE WINDOW BY 15.625 %
;
        MOV     R1,#STATUS              ;POINT TO RESPIRATION STATUS
        MOV     A,@R1                   ;GET RESP STATUS
        JB0     JMPDET                  ;IF NOT 1st TIME SINCE GOING NEG ? JUMP
        ORL     A,#00000001B            ;ELSE INDICATE 1ST TIME THROUGH
        MOV     @R1,A                   ;SAVE NEW RESP STATUS
        MOV     R5,#28H                 ;SET MULTIPLICAND = 296
        MOV     R6,#01H                 ;
        CALL    FIXTHS                  ;CALL ROUTINE TO FIND "NEW" WINDOW
JMPDET  JMP     DETECT                  ;GOTO DETECT BREATH
;
; COMPARE 1/4 RESPIRATION DATA WITH NEGATIVE AUTO THRESHOLD ?
;
NEGTST  INC     R0                      ;POINT TO NEG AUTO THRESHOLD
        MOV     A,@R0                   ;GET NEG AUTO THRESHOLD
        CPL     A                       ;COMPLEMENT IT
        INC     A                       ;AND ADD 1 TO IT
        ADD     A,@R1                   ;ADD 1/4 RESP DATA TO IT
        JC      DETECT                  ;IF 1/4 DATA > NEG THRESHOLD ? JUMP
;
; NEG AUTO THRESHOLD = 1/4 DATA
; POS AUTO THRESHOLD = POS AUTO THRESHOLD - "NEW" DIFFERENCE
;
        MOV     R2,A                    ;SAVE DIFFERENCE OF NEG AUTO - 1/4 DATA
```

```
            MOV     A,@R1            ;RECALL 1/4 RESP DATA
            MOV     @R0,A            ;SAVE AS "NEW" NEG AUTO THRESHOLD
            DEC     R0               ;POINT TO POS AUTO THRESHOLD
            MOV     A,@R0            ;GET POS AUTO THRESHOLD
            ADD     A,R2             ;ADD DIFFERENCE OF NEG AUTO - 1/4 DATA
            MOV     @R0,A            ;SAVE SUM AS "NEW" POS AUTO THRESHOLD
;
; INDICATE DATA WHENT BELOW NEG AUTO THRESHOLD
;
            MOV     R1,#STATUS       ;POINT TO RESP STATUS
            MOV     A,@R1            ;GET RESP STATUS
            ANL     A,#11111110B     ;INDICATE 1/4 DATA < NEG AUTO
            MOV     @R1,A            ;SAVE NEW RESP STATUS
;
; COMPARE OUTPUT OF FILTER WITH POSITIVE DETECT THRESHOLD
;
DETECT      MOV     R0,#DADATA       ;POINT TO LSB OF FILTERED DATA
            MOV     R1,#PTHRES       ;POINT TO LSB OF POS DETECT THRESHOLD
            CALL    COMP2            ;COMPARE THE TWO 16 BIT VALUES
            JC      INHALE           ;IF DATA >= POS THRES ? JUMP
            JMP     EXHALE           ;ELSE DATA < POS THRES ? JUMP
;
; IF DATA > POSITIVE DETECT THRESHOLD ? THEN RAISE BOTH THRESHOLDS
;
INHALE      MOV     R0,#NTHRES       ;POINT TO LSB OF NEG THRESHOLD
            CALL    ADJUST           ;SET POS THRES = DATA, NEG = NEG + DIFF
;
; INDICATE RESPIRATION DATA > THE POSITIVE DETECT THRESHOLD
;
            MOV     R0,#STATUS       ;POINT TO CURRENT SLOPE STATUS
            MOV     A,@R0            ;GET BREATH SLOPE STATUS
            ANL     A,#11111101B     ;INDICATE DATA > POS DETECT THRES.
            MOV     @R0,A            ;SAVE AS NEW SLOPE STATUS
            JMP     BINTST           ;GOTO TEST BR-BR INTERVAL > 1.2 SEC
;
; ELSE COMPARE OUTPUT OF FILTER WITH NEGATIVE DETECT THRESHOLD
;
EXHALE      DEC     R0               ;POINT TO LSB OF FILTERED DATA
            INC     R1               ;POINT TO LSB OF NEG DETECT THRESHOLD
            CALL    COMP2            ;COMPARE THE TWO 16 BIT VALUES
            JC      BINTST           ;IF DATA > NEG THRES ? JUMP
;
; IF DATA < NEGATIVE DETECT THRESHOLD ? THEN LOWER BOTH THRESHOLDS
;
NSLOPE      MOV     R0,#PTHRES       ;POINT TO LSB OF POS THREHSOLD
            CALL    ADJUST           ;SET NEG THRES = DATA, POS = POS - DIFF
;
; IF 1ST TIME DATA < NEGATIVE DETECT THRESHOLD ?
;
            MOV     R0,#STATUS       ;POINT TO CURRENT SLOPE STATUS
            MOV     A,@R0            ;GET CURRENT SLOPE STATUS
            JB1     BINTST           ;IF NOT 1st TIME SINCE GOING POS ? JUMP
            MOV     R1,#BBINT        ;POINT TO BR-BR INTERVAL COUNTER
            MOV     A,@R1            ;GET BR-BR INTERVAL COUNT
            ADD     A,#0F0H          ;ADD -16 TO BR-BR INTERVAL
            JNC     COMCVA           ;IF BR-BR INTERVAL < .32 SEC ? JUMP
            MOV     A,@R0            ;RECALL CURRENT SLOPE STATUS
            ORL     A,#00000010B     ;ELSE INDICATE 1ST TIME SINCE POS
            MOV     @R0,A            ;SAVE AS NEW SLOPE STATUS
;
; SEE BR-BR INTERVAL = .5 SEC +- 5% (FOR SELF TEST)
;
            INC     R0               ;POINT TO SELF TEST STATUS
```

```
                MOV     A,@R1              ;ELSE RECALL BR-BR INTERVAL
                ADD     A,#0E3H            ;ADD -29 TO IT
                JC      NOBRTH             ;IF INTERVAL > .58 SEC, JUMP
                ADD     A,#007H            ;ADD 7 TO IT
                JNC     NOBRTH             ;IF INTERVAL < .42 SEC, JUMP
                MOV     A,@R0              ;GET CURRENT SELF TEST STATUS
                ORL     A,#00000001B       ;SET BR=120 INDICATOR
                JMP     SVBRST             ;GOTO SAVE SELF TEST STATUS
NOBRTH          MOV     A,@R0              ;RECALL CURRENT SELF TEST STATUS
                ANL     A,#11111110B       ;SET BR <> 120 INDICATOR
SVBRTH          MOV     @R0,A              ;SAVE AS CURRENT SELF TEST STATUS
                MOV     A,#0FBH            ;SET ACCUM = -5
                MOV     R1,#BRLED          ;SET BREATH LED COUNTER
                MOV     @R1,A              ;TO 5 COUNTS = 100 mS DURATION
                MOV     R1,#BREATH         ;POINT TO BREATH INDICATOR
                MOV     @R1,A              ;INDICATE BREATHS FOR INTERRUPT
;
; SEE IF RESP AMPLITUDE = 1 ohm +-20% ?
;
                MOV     R1,#MINWAV         ;POINT TO MINIMUM WAVE VALUE
                MOV     A,@R1              ;GET MINIMUM WAVE VALUE
                MOV     @R1,#0FFH          ;SET MINIMUM WAVE VALUE = +FULL SCALE
                CPL     A                  ;COMPLEMENT MIN VALUE
                INC     A                  ;AND ADD 1 TO IT
                INC     R1                 ;POINT TO MAXIMUM WAVE VALUE
                ADD     A,@R1              ;ADD MAX WAVE VALUE TO - MIN WAVE VALUE
                MOV     @R1,#000H          ;SET MAXIMUM WAVE VALUE = -FULL SCALE
                ADD     A,#0D9H            ;ADD -39 TO DIFF
                JC      NO1OHM             ;IF DIFF > 1.2 OHMS ? JUMP
                ADD     A,#00EH            ;ADD 14 TO DIFF
                JNC     NO1OHM             ;IF DIFF < .8 OHMS ? JUMP
                MOV     A,@R0              ;RECALL CURRENT SELF TEST STATUS
                ORL     A,#00000010B       ;INDICATE DIFF IS .8 TO 1.2 OHMS
                JMP     SVOHST             ;GOTO SAVE 1 OHM PASS/FAIL STATUS
NO1OHM          MOV     A,@R0              ;RECALL CURRENT SELF TEST STATUS
                ANL     A,#11111101B       ;INDICATE DIFF IS NOT .8 TO 1.2 OHMS
SVOHST          MOV     @R0,A              ;SAVE AS SELF TEST STATUS
;
; SEE IF BR-BR INTERVAL > 0.6 SEC ? IF SO CLEAR BREATH SELF TEST BITS
;
BINTST          MOV     R0,#BBINT          ;POINT TO BR-BR INTERVAL
                MOV     A,@R0              ;GET BR-BR INTERVAL COUNTER
                ADD     A,#0C8H            ;ADD -55 TO IT
                JNC     COMCVA             ;IF BR-BR INTERVAL < 1.2 SEC ? JUMP
                MOV     R0,#TSTAT          ;POINT TO SELF TEST STATUS
                MOV     A,@R0              ;GET SELF TEST STATUS
                ANL     A,#11111100B       ;CLEAR BR=60,RESP = 1 OHM BITS
                MOV     @R0,A              ;SAVE AS SELF TEST STATUS
;
;SUBTRACT 256 FORM OUTPUT OF CVA FILTER AND MULTIPLY BY 128
;
COMCVA          MOV     R0,#DADATA+1       ;POINT TO MSB OF CVA DATA
                MOV     A,@R0              ;GET MSB OF CVA DATA
                JZ      MINCVA             ;IF CVA DATA < 256 ? JUMP
                ADD     A,#0FDH            ;ELSE ADD -3 TO IT
                JZ      MAXCVA             ;IF CVA DATA > 768 ? JUMP
                ADD     A,#002H            ;ELSE ADD 2 TO IT
                MOV     @R0,A              ;SAVE AS LIMITED MSB
                DEC     R0                 ;POINT TO LSB OF CVA DATA
                MOV     R7,#007H           ;SET LOOP COUNTER = 7
                CALL    ROTLFT             ;CALL ROUTINE TO ROTATE CVA DATA LEFT
                JMP     COMNUM             ;GOTO COMPUTE # OF INTERRUPTS
;
```

```
; LIMIT (OUTPUT OF CVA FILTER - 256) * 128 TO MINIMUM VALUE
;
MINCVA  DEC     R0              ;POINT TO LSB OF CVA DATA
        CALL    CLRTWO          ;CLEAR CVA DATA
        JMP     COMNUM          ;GOTO COMPUTE # OF INTERRUPTS
;
; LIMIT (OUTPUT OF CVA FILTER - 256) * 128 TO MAXIMUM VALUE
;
MAXCVA  MOV     @R0,#0FFH       ;SET MSB OF CVA DATA = MAX VALUE
        DEC     R0              ;POINT TO LSB OF CVA DATA
        MOV     @R0,#0C0H       ;SET LSB OF CVA DATA = MAX VALUE
;
; DIVIDE 3000/HR TO GET # OF 2mSEC INTERRUPTS BETWEEN RESP SAMPLES
;
COMNUM  MOV     R0,#SAMPLE      ;POINT TO LIMITED HR (60-180)
        MOV     A,@R0           ;GET ADJUSTED HR
        MOV     R6,A            ;SAVE AS LSB OF DIVISOR
        MOV     R7,#00H         ;SET MSB OF DIVISOR = 0
        MOV     R2,#0B8H        ;SET DIVIDEND = 3000
        MOV     R3,#00BH        ;
        CALL    DIVIDE          ;DIVIDE 3000/LIMITED HR
;
; FIND DIFFERENCE BETWEEN PRESENT CVA DATA - NEW CVA DATA
;
        MOV     R0,#DADATA      ;POINT TO LSB OF PRESENT CVA DATA
        MOV     R1,#NEWCVA      ;POINT TO LSB OF NEW CVA DATA
        CALL    COMP2           ;SUBTRACT PRESENT - NEW CVA DATA
        JZ      ZERDIF          ;IF PRESENT - NEW = 0 ? JUMP
        JC      POSDEL          ;IF PRESENT >= NEW CVA ? JUMP
;
; IF NEGATIVE, THEN FIND DIFFERENCE BETWEEN NEW - PRESENT CVA DATA
;
NEGDIF  MOV     R0,#NEWCVA      ;POINT TO LSB OF NEW CVA DATA
        MOV     R1,#DADATA      ;POINT TO MSB OF PRESENT CVA DATA
        CALL    COMP2           ;SUBTRACT NEW - PRESENT CVA DATA
;
; DIVIDE THE ABSOLUTE DIFFERENCE BY NUMBER OF 2mSEC NTERRUPTS
;
        CALL    FDELTA          ;DIVIDE DIFF/# 2mSEC INTERRUPTS
        CPL     A               ;COMPLEMENT QUOTIENT
        MOV     R3,#0FFH        ;SET MSB OF DELTA = -1
        JMP     SAVDEL          ;GOTO SAVE BOTH BYTES OF DELTA
;
; TEST FOR DIFFERENCE BETWEEN PRESENT - NEW > 0
;
POSDEL  CALL    FDELTA          ;DIVIDE DIFF/# 2mSEC INTERRUPTS
        INC     A               ;MAKE LSB OF DELTA = 1
ZERDIF  MOV     R3,#000H        ;SET MSB OF DELTA = 0
;
; SAVE ENTIRE VALUE OF DELTA DIFFERENCE
;
SAVDEL  MOV     R2,A            ;SAVE LSB OF DELTA
        MOV     R0,#UPSTAT      ;POINT TO UPDATE STATUS
        MOV     @R0,#10000000B  ;INDICATE UPDATING CVA DATA
        MOV     R0,#DELTA+1     ;POINT TO LSB OF DELTA
        MOV     R7,#004H        ;SET LOOP COUNTER = 4
        CALL    ROTLOP          ;MULTIPLY DELTA * 128
;
; SET NEW CVA DATA = PRESENT CVA DATA
;
        MOV     R0,#DADATA      ;POINT TO LSB OF PRESENT CVA DATA
        MOV     R1,#NEWCVA      ;POINT TO MSB OF NEW CVA DATA
        CALL    MOVTWO          ;MOVE CURRENT INTO NEW CVA DATA
```

```
        MOV     R0,#UPSTAT          ;POINT TO UPDATE STATUS
        MOV     @R0,#000H           ;CLEAR UPDATE STATUS
;
; COMPUTE CURRENT BEAT-to-BEAT HEART RATE VALUE FOR D/A OUTPUT
;
        MOV     R0,#HRATE           ;POINT TO CURRENT BEAT-BEAT HR
        MOV     A,@R0               ;GET CURRENT BEAT-BEAT HR
        MOV     R4,A                ;SAVE FOR LATTER
        ADD     A,#00FH             ;ADD -240 TO IT
        JNC     SUB40               ;IF HR <= 240 ? JUMP
        MOV     R4,#0F0H            ;ELSE SET OUTPUT HR = 240
SUB40   MOV     A,R4                ;RECALL OUTPUT HR
        ADD     A,#0D8H             ;ADD -40 TO IT
        MOV     R4,A                ;SAVE AS OUTPUT HR
        JC      MULTHR              ;IF BEAT-BEAT HR > 40 ? JUMP
        MOV     R4,#000H            ;ELSE SET SET OUTPUT HR = 0
MULTHR  MOV     R5,#047H            ;SET MULTIPLICAND = 327
        MOV     R6,#001H            ;
        CALL    MULT                ;(HR-40) * 327 / 64
        MOV     R0,#HRDA            ;POINT TO LSB OF HR D/A VALUE
        MOV     A,R1                ;GET LSB OF PRODUCT
        ADD     A,#020H             ;ADD 32 TO IT
        MOV     @R0,A               ;SAVE AS LSB OF HR D/A VALUE
        INC     R0                  ;POINT TO MSB OF HR D/A VALUE
        MOV     A,R2                ;GET MSB OF PRODUCT
        ADDC    A,#000H             ;ADD ABOVE CARRY TO IT
        MOV     @R0,A               ;SAVE AS MSB OF HR D/A VALUE
;
; CONTINUE TO LOOP WAITING FOR NEXT RESPIRATION SAMPLE
;
        JMP     LOOP                ;CONTINUE TO LOOP
;
        END
!!
        NAME    MATH
;
;**********************
;* VARIABLE DEFINITION *
;**********************
;
DAMEM   EQU     001H
HRATE   EQU     020H
HRAVG   EQU     021H
INSTAT  EQU     023H
TSTAT   EQU     025H
BTIMER  EQU     028H
TTIMER  EQU     029H
APMAX   EQU     02CH
HRDA    EQU     034H
OLDHR   EQU     036H
DADATA  EQU     038H
SAMPLE  EQU     043H
STAGE   EQU     05FH
DELAY   EQU     060H
WINDOW  EQU     071H
NAUTO   EQU     073H
PTHRES  EQU     074H
NTHRES  EQU     076H
NUMBER  EQU     078H
ANSWER  EQU     07CH
PORTA   EQU     0C0H
PORTB   EQU     0C1H
```

```
PORTC     EQU       0C2H
CLEARA    EQU       0C8H
SETA      EQU       0CCH
LSBT0     EQU       0D0H
START0    EQU       0D5H
CRT0      EQU       0D8H
;
;**************************
;* DECLARE ROUTINE NAMES *
;**************************
;
          GLOBAL    SAMHLD
          GLOBAL    ROTLFT
          GLOBAL    ROTLOP
          GLOBAL    ROLEFT
          GLOBAL    FSHLED
          GLOBAL    FDELTA
          GLOBAL    CLRTWO
          GLOBAL    OUTDA
          GLOBAL    INCSEC
          GLOBAL    SAVEHR
          GLOBAL    ADJUST
          GLOBAL    MOVTWO
          GLOBAL    TWOADD
          GLOBAL    DECTHS
          GLOBAL    FIXTHS
          GLOBAL    SHIFT
          GLOBAL    COMP2
          GLOBAL    ALRMTST
          GLOBAL    FILTER
          GLOBAL    FILRET
          GLOBAL    DIVIDE
          GLOBAL    MULT
          GLOBAL    SAMINT
          GLOBAL    GROUPA
;
; DECLARATION OF MODULE SPACE ALLOCATION
;
          SECTION   ROUT,ABSOLUTE
          ORG       42AH
;
; ROUTINE TO WAIT 15 uSEC AND THEN RE-ENABLE CHANNEL 0 OF DG211
;
SAMHLD    CLR       F0                    ;CLEAR LEADS OFF FLAG
          MOV       R1,#PORTB             ;POINT TO PORT B INPUT
          MOVX      A,@R1                 ;INPUT PORT B STATUS
          MOV       R5,A                  ;SAVE IN REG 5
          ANL       P2,#00111111B         ;ENABLE CHANNEL 0 OF DG211
          RET                             ;RETURN
;
; ROUTINE TO ROTATE LEFT VALUE IN R2 (LSB) AND R3 (MSB) R7 TIMES
;
ROTLFT    MOV       A,@R0                 ;GET LSB OF VALUE
          MOV       R2,A                  ;SAVE FOR ROTATE
          INC       R0                    ;POINT TO MSB OF VALUE
          MOV       A,@R0                 ;GET MSB OF VALUE
          MOV       R3,A                  ;SAVE FOR LATTER
ROTLOP    CALL      ROLEFT                ;ROTATE R2,R3 LEFT R7 TIMES
          JMP       SAVDAT                ;GOTO SAVE R2,R3 IN R0
;
; ROTATE CONTENTS OF R2 (LSB) & R3 (MSB) LEFT R7 TIMES
;
ROLEFT    CLR       C                     ;CLEAR CARRY
```

```
            MOV     A,R2            ;GET LSB OF VALUE
            RLC     A               ;ROTATE LSB OF VALUE LEFT ONCE
            MOV     R2,A            ;SAVE AS LSB OF VALUE
            MOV     A,R3            ;GET MSB OF VALUE
            RLC     A               ;ROTATE MSB OF VALUE LEFT ONCE
            MOV     R3,A            ;SAVE AS MSB OF VALUE
            DJNZ    R7,ROLEFT       ;LOOP HERE R7 TIMES
            RET                     ;RETURN
;
; ROUTINE TO OUTPUT NEXT LED SEQUENCE AND BEEP AUDIO DURING LAST LED
;
FSHLED      IN      A,P1            ;INPUT LAST LED OUTPUT
            RL      A               ;ROTATE RIGHT ONCE
            OUT     P1,A            ;ELSE OUTPUT NEW FLASH OUTPUT
            MOV     R0,#CLEARA      ;POINT TO CLEAR BIT IN PORT A
            JB7     OUTBEP          ;IF BIT 7 SET ? JUMP
            JMP     NOBEEP          ;GO TO END OF FLASH ROUTINE
OUTBEP      MOV     R0,#SETA        ;POINT TO SET BIT IN PORT A
NOBEEP      MOV     A,#00100000B    ;SET AUDIO ENABLE BIT
            MOVX    @R0,A           ;OUTPUT CURRENT AUDIO TONE
            RET                     ;RETURN
;
; ROUTINE TO OBTAIN AND STORE BRADYCARDIA, TACHYCARDIA & APNEA LIMITS
;
ATABLE      BYTE    10, 30, 25, 20, 15, 10, 10, 10
BTABLE      BYTE    90, 80, 70, 60, 50, 40, 30,100
TTABLE      BYTE    240,220,200,180,160,140,120,255
;
GETLIM      MOVX    A,@R0           ;INPUT PORT STATUS
            ANL     A,#00000111B    ;MASK IN 3 LSB BITS
            ADD     A,R1            ;ADD TO START OF LIMIT TABLE
            MOVP    A,@A            ;GET ALARM LIMIT FROM TABLE
            MOV     R2,A            ;SAVE IN R2 FOR LATTER
            MOV     R3,A            ;SAVE IN R3 FOR LATTER
            MOV     R0,#HRAVG       ;POINT TO CURRENT HR AVERAGE
            MOV     A,@R0           ;GET CURRENT HR AVERAGE
            RET                     ;RETURN
;
; ROUTINE TO TEST FOR APNEA, BRADYCARDIA AND TACHYCARDIA ALARMS
;
ALRMTST     MOV     R0,#PORTC       ;POINT TO PORT C INPUT STATUS
            MOV     R1,#ATABLE      ;POINT TO APNEA TABLE
            CALL    GETLIM          ;CALL ROUTINE TO GET BRADY LIMIT
            MOV     A,R2            ;RECALL APNEA LIMIT
            MOV     R0,#APMAX       ;POINT TO MAXIMUM APNEA LIMIT
            ADD     A,#007H         ;ADD 7 TO APENA LIMIT
            MOV     @R0,A           ;SAVE AS MAXIMUM APNEA LIMIT
            MOV     A,R2            ;RECALL APNEA LIMIT
            CPL     A               ;COMPLEMENT IT
            INC     A               ;INCREMENT IT BY 1
            DEC     R0              ;POINT TO MSB OF APNEA COUNTER
            ADD     A,@R0           ;ADD -LIMIT TO APNEA COUNTER
            MOV     R4,#00010000B   ;SET-UP ALARM TEST BIT
            MOV     R1,#INSTAT      ;POINT TO CURRENT ALARM STATUS
            CALL    ALRCHK          ;CALL ALARM TEST ROUTINE
            MOV     R0,#PORTB       ;POINT TO PORT B INPUT STATUS
            MOV     R1,#BTABLE      ;POINT TO BRADY TABLE
            CALL    GETLIM          ;CALL ROUTINE TO GET BRADY LIMIT
            MOV     R3,A            ;SAVE CURRENT HR AVERAGE FOR LATTER
            MOV     R0,#BTIMER      ;POINT TO BRADY DELAY TIMER
            MOV     R4,#00000010B   ;SET-UP ALARM TEST BIT
            CALL    ALRTST          ;CALL ALARM TEST ROUTINE
            MOV     R0,#PORTA       ;POINT TO PORT A INPUT STATUS
```

```
                MOV     R1,#TTABLE          ;POINT TO TACHY TABLE
                CALL    GETLIM              ;CALL ROUTINE TO GET TACHY LIMIT
                MOV     R2,A                ;SAVE CURRENT HR AVERAGE FOR LATTER
                MOV     R0,#TTIMER          ;POINT TO TACHY DELAY TIMER
                MOV     R4,#00000100B       ;SET-UP ALARM TEST BIT
ALRTST          MOV     R1,#INSTAT          ;POINT TO CURRENT ALARM STATUS
                MOV     A,R3                ;GET "B" VALUE
                CPL     A                   ;COMPLEMENT "B" VALUE
                INC     A                   ;AND ADD 1 TO IT
                ADD     A,R2                ;ADD "A" VALUE
                JNC     ALROF               ;IF "A" VALUE < "B" VALUE ? JUMP
                MOV     A,@R0               ;ELSE, GET DELAY TIMER
                ADD     A,#038H             ;ADD -200 TO IT
                JZ      ALRON               ;IF TIMER ALREADY = 4 SEC ? JUMP
                INC     @R0                 ;ELSE INCREMENT DELAY TIMER BY 1
                RET                         ;RETURN
ALRCHK          JNC     ALROFF              ;IF COUNT < LIMIT ? JUMP
ALRON           IN      A,P1                ;INPUT CURRENT LED STATUS
                ORL     A,R4                ;MASK IN NEW LED STATUS
                OUTL    P1,A                ;OUTPUT NEW LED STATUS
                MOV     A,R4                ;RECALL CURRENT ALARM BIT
                ORL     A,@R1               ;SET ALARM BIT IN STATUS WORD
                MOV     @R1,A               ;SAVE AS NEW ALARM STATUS
                RET                         ;RETURN FROM ALARM TEST
ALROF           MOV     @R0,#000H           ;RESET DELAY TIMER TO ZERO
ALROFF          MOV     A,R4                ;RECALL ALARM BIT
                CPL     A                   ;COMPLEMENT IT
                ANL     A,@R1               ;CLEAR ALARM BIT IN STATUS WORD
                MOV     @R1,A               ;SAVE AS NEW ALARM STATUS
                RET                         ;RETURN FROM ALARM TEST
;
; ROUTINE TO SAVE B-B HR (ACCUM) AND SET-UP RESPIRATION SAMPLE COUNT
;
SAVEHR          MOV     R0,#HRATE           ;POINT TO BEAT-to-BEAT HEART RATE
                MOV     A,R7                ;RECALL COMPUTED BEAT-to-BEAT HR
                MOV     @R0,A               ;SAVE PRESENT BEAT-to-BEAT HEART RATE
                MOV     R0,#TSTAT           ;POINT TO SELF TEST STATUS
                ADD     A,#00AH             ;ADD -246 TO IT
                JC      NOETST              ;IF HR > 246 ? JUMP
                ADD     A,#00BH             ;ELSE ADD 11 TO HR
                JNC     NOTEST              ;IF HR < 234 ? JUMP
                MOV     A,@R0               ;RECALL SELF TEST STATUS
                ORL     A,#00000100B        ;SET HR=240 BIT
                JMP     SVSFST              ;GOTO SAVE STATUS
NOTEST          MOV     A,@R0               ;RECALL SELF TEST STATUS
                ANL     A,#11111011B        ;CLEAR HR=240 BIT
SVSFST          MOV     @R0,A               ;SAVE AS NEW SELF TEST STATUS
                MOV     A,R7                ;RECALL BEAT-to-BEAT HEART RATE
                ADD     A,#04BH             ;IF HR < 180 BPM ?
                JNC     HROK                ;THEN JUMP AROUND
                MOV     R7,#0B4H            ;ELSE SET HR SAMPLE COUNT = 180
HROK            MOV     A,R7                ;RECALL HR SAMPLE COUNT
                MOV     R0,#SAMPLE          ;POINT TO HR SAMPLE COUNT
                MOV     @R0,A               ;SAVE AS "NEW" HR SAMPLE COUNT
                RET                         ;RETURN
;
; OUTPUT DATA IN REG R0 TO D/A IN 2 BYTES
;
OUTDA           MOV     R1,#DAMEM           ;POINT TO BYTE 1 OF D/A
                MOV     A,@R0               ;GET MSB OF OUTPUT DATA
                MOVX    @R1,A               ;OUTPUT TO BYTE 1 OF D/A
                DEC     R0                  ;POINT TO LSB OF OUTPUT DATA
                INC     R1                  ;POINT TO BYTE 2 OF D/A
```

```
        MOV     A,@R0           ;GET LSB OF OUTPUT DATA
        MOVX    @R1,A           ;OUTPUT TO BYTE 2 OF D/A
        RET                     ;RETURN
;
; ROUTINE TO INCREMENT 2 BYTE VALUE - 1 BYTE = 20 mSec, 2 BYTE = 1 sec
;
INCSEC  INC     @R0             ;INCREMENT LSB OF COUNTER BY 20 mSec
        MOV     A,@R0           ;GET LSB OF COUNTER
        ADD     A,#0CEH         ;ADD -50 TO IT
        JNZ     ENDSEC          ;IF COUNT < 50 ? THEN JUMP
        MOV     @R0,A           ;ELSE SET LSB OF COUNTER = 0
        INC     R0              ;POINT TO MSB OF COUNTER
        INC     @R0             ;INCREMENT MSB OF COUNTER BY 1 Sec
        RET                     ;RETURN W/ R0 POINTING TO MSB OF COUNT
ENDSEC  INC     R0              ;POINT TO MSB OF COUNTER
        RET                     ;RETURN
;
; ROUTINE TO CLEAR 2 CONSECTIVE BYTES POINTED TO BY R0
;
CLRTWO  CLR     A               ;CLEAR ACCUM
        MOV     @R0,A           ;CLEAR 1ST BYTE POINTED TO BY R0
        INC     R0              ;POINT TO 2ND BYTE OF R0
        MOV     @R0,A           ;CLEAR 2ND BYTE POINTER TO BY R0
        RET                     ;RETURN
;*****************************************************
;*              DIGITAL FILTER ROUTINE                *
;*                                                    *
;* NUMBER+0            8 LSB BITS OF Z-1              *
;* NUMBER+1            8 MSB BITS OF Z-1              *
;* NUMBER+2            8 LSB BITS OF Z-2              *
;* NUMBER+3            8 MSB BITS OF Z-2              *
;*****************************************************
;
FILTER  CALL    FIXRESP         ;ADJUST INPUT DATA FOR MATH
FILLOP  MOV     R0,#DELAY       ;POINT TO SOURCE ADDRESS
        MOV     R1,#STAGE       ;POINT TO STAGE INDICATOR
        MOV     A,@R1           ;GET STAGE INDICATOR
        RL      A               ;MULTIPLY POINTER BY 4
        RL      A               ;BY ROTATING
        ADD     A,R0            ;ADD TO START OF DESTINATION
        MOV     R0,A            ;SAVE DESTINATION ADDRESS
        MOV     R1,#NUMBER      ;POINT TO DESTINATION ADDRESS
        CALL    MOVE            ;MOVE 4 BYTES FROM DELAY TO NUMBER
;
; MULTIPLY COEF "A" * Z-1
;
        CALL    XCOEFA          ;MULTIPLY Z-1 * COEF "A"
;
; SAVE 32 BIT RESULTS IN "ANSWER" (4 BYTE NUMBER)
;
        MOV     R0,#ANSWER      ;POINT TO BYTE 0 OF ANSWER
        MOV     A,R1            ;GET BYTE 0 OF RESULTS
        MOV     @R0,A           ;SAVE AS BYTE 0 OF ANSWER
        INC     R0              ;POINT TO BYTE 1 OF ANSWER
        MOV     A,R2            ;GET BYTE 1 OF RESULTS
        MOV     @R0,A           ;SAVE AS BYTE 1 OF ANSWER
        INC     R0              ;POINT TO BYTE 2 OF ANSWER
        MOV     A,R3            ;GET BYTE 2 OF RESULTS
        MOV     @R0,A           ;SAVE AS BYTE 2 OF ANSWER
        INC     R0              ;POINT TO BYTE 3 OF ANSWER
        CLR     A               ;CLEAR ACCUM
        MOV     @R0,A           ;SAVE AS BYTE 3 OF ANSWER
```

```
;
; "ANSWER" = "ANSWER" + (ORIGINAL Z-1 32 BIT * 245)
;
        MOV     R0,#ANSWER+1        ;POINT TO BYTE 1 OF ANSWER
        MOV     R1,#NUMBER          ;POINT TO BYTE 0 OF ORIGINAL Z-1
        CALL    DADD                ;CALL ROUTINE TO ADD THE TWO
;
; "ANSWER" = "ANSWER" + INPUT DATA (10 BIT NUMBER)
;
        MOV     R0,#ANSWER+1        ;POINT TO BYTE 1 OF ANSWER
        MOV     R1,#DATATA          ;POINT TO BYTE 0 OF INPUT
        CALL    DADD                ;CALL ROUNTINE TO ADD THE TWO
;
; MULTIPLY COEF "B" * Z-2
;
        CALL    XCOEFB              ;MULTIPLY Z-2 * COEF "B"
;
; MAKE THE RSULTING PRODUCT NEGATIVE BY 2'S COMPLEMENT
;
        MOV     A,R1                ;GET BYTE 0 OF ABOVE PRODUCT
        CPL     A                   ;COMPLEMENT
        ADD     A,#01H              ;AND ADD 1 TO IT
        MOV     R1,A                ;SAVE AS BYTE 0 - PRODUCT
        MOV     R2,A                ;GET BYTE 1 OF ABOVE PRODUCT
        CPL     A                   ;COMPLEMENT IT
        ADDC    A,#00H              ;ADD CARRY TO IT
        MOV     R2,A                ;SAVE AS BYTE 1 - PRODUCT
        MOV     R3,A                ;GET BYTE 2 OF ABOVE PRODUCT
        CPL     A                   ;COMPLEMENT IT
        ADDC    A,#00H              ;ADD CARRY TO IT
        MOV     R3,A                ;SAVE AS BYTE 2 OF - PRODUCT
        MOV     A,#0FFH             ;MAKE ACCUM = 0FFH
        ADDC    A,#00H              ;ADD CARRY TO BYTE 3 OF PRODUCT
        MOV     R4,A                ;SAVE AS BYTE 3 OF - PRODUCT
;
; "ANSWER" = "ANSWER" + MINUS PRODUCT
;
        MOV     R0,#ANSWER          ;POINT TO BYTE 0 OF ANSWER
        MOV     A,R0                ;GET BYTE 0 OF ANSWER
        ADD     A,#R1               ;AND BYTE 0 OF - PRODUCT
        MOV     @R0,A               ;SAVE AS BYTE 0 OF ANSWER
        INC     R0                  ;POINT TO BYTE 1 OF ANSWER
        MOV     A,@R0               ;GET BYTE 1 OF ANSWER
        ADDC    A,R2                ;ADD BYTE 1 OF - PRODUCT
        MOV     @R0,A               ;SAVE AS BYTE 1 OF ANSWER
        INC     R0                  ;POINT TO BYTE 2 OF ANSWER
        MOV     A,@R0               ;GET BYTE 2 OF ANSWER
        ADDC    A,R3                ;ADD BYTE 2 OF - PRODUCT
        MOV     @R0,A               ;SAVE AS BYTE 2 OF ANSWER
        INC     R0                  ;POINT TO BYTE 3 OF ANSWER
        MOV     A,@R0               ;GET BYTE 3 OF ANSWER
        ADDC    A,R4                ;ADD BYTE 3 OF - PRODUCT
        MOV     @R0,A               ;SAVE AS BYTE 3 OF ANSWER
;
; IF THE SUM OF "ANSWER" + MINUS PRODUCT > 0 ? THEN GOTO DIVIDE BY 256
;
        JC      SUMOK               ;IF CARRY THEN >= 0
        ANL     A,#80H              ;MASK IN SIGN BIT
        JZ      SUMOK               ;IF SIGN BIT LOW THEN POSITIVE
;
; ELSE SET SUM ("ANSWER") = 0
;
        CLR     A                   ;CLEAR ACCUM
```

```
            MOV     R3,#04H         ;ELSE SET LOOP COUNTER = 4
            MOV     R6,A            ;SAVE FOR LSB OF Z-1 LATTER
            MOV     R7,A            ;SAVE FOR MSB OF Z-1 LATTER
            MOV     R0,#ANSWER      ;POINT TO BYTE 1 OF ANSWER
CLOOP       MOV     @R0,A           ;CLEAR CURRENT BYTE
            INC     R0              ;POINT TO NEXT BYTE
            DJNZ    R3,CLOOP        ;LOOP THROUGH ALL 3 BYTES
            JMP     FEEDF           ;GOTO FIND FEED FORWARD SUM
;
; IF SUM IS > 0 THEN DIVIDE "ANSWER" BY 256
;
SUMOK       MOV     R0,#ANSWER      ;POINT TO BYTE 0 OF ANSWER
            MOV     R1,#ANSWER+1H   ;POINT TO BYTE 1 OF ANSWER
            MOV     A,@R1           ;GET BYTE 1 OF ANSWER
            MOV     @R0,A           ;SAVE AS BYTE 0 OF ANSWER
            MOV     R6,A            ;SAVE AS LSB OF FEED BACK
            INC     R0              ;POINT TO BYTE 1 OF ANSWER
            INC     R1              ;POINT TO BYTE 2 OF ANSWER
            MOV     A,@R1           ;GET BYTE 2 OF ANSWER
            MOV     @R0,A           ;SAVE AS BYTE 1 OF ANSWER
            MOV     R7,A            ;SAVE AS MSB OF FEED BACK
            CLR     A               ;CLEAR ACCUM
            MOV     @R1,A           ;CLEAR BYTE 2 OF ANSWER
;
; "ANSWER" = "ANSWER" + ( 2 * Z-1 )
;
FEEDF       CALL    Z1ADD           ;CALL ROUTINE TO ADD Z-1 TO SUM
            CALL    Z1ADD           ;CALL ROUTINE TO ADD Z-1 TO SUM
;
; "ANSWER" = "ANSWER" + Z-2
;
            MOV     R1,#NUMBER+2    ;POINT TO LSB OF Z-2
            CALL    Z2ADD           ;CALL ROUTINE TO ADD Z-2 TO SUM
;
; SET Z-2 = Z-1
;
            MOV     R0,#NUMBER      ;POINT TO LSB OF Z-1
            MOV     R1,#NUMBER+2    ;POINT TO LSB OF Z-2
            CALL    MOVTWO          ;MOVE 2 BYTES FROM R0 TO R1
;
; SET Z-1 = "FEED BACK SUM"
;
            MOV     R0,#NUMBER      ;POINT TO LSB OF Z-1
            MOV     A,R6            ;RECALL LSB OF SUM
            MOV     @R0,A           ;SAVE AS LSB OF Z-1
            INC     R0              ;POINT TO MSB OF Z-1
            MOV     A,R7            ;RECALL MSB OF SUM
            MOV     @R0,A           ;SAVE AS MSB OF Z-1
;
; "ANSWER" = "ANSWER" / 4
;
            MOV     R3,#02H         ;SET LOOP COUNTER = 2
DIVBY4      MOV     R0,#ANSWER+2    ;POINT TO MSB OF ANSWER
            CLR     C               ;CLEAR CARRY
            MOV     A,@R0           ;GET MSB OF ANSWER
            RRC     A               ;ROTATE RIGHT ONCE
            MOV     @R0,A           ;SAVE AS MSB OF ANSWER
            DEC     R0              ;POINT TO XSB OF ANSWER
            MOV     A,@R0           ;GET XSB OF ANSWER
            RRC     A               ;ROTATE RIGHT ONCE
            MOV     @R0,A           ;SAVE AS XSB OF ANSWER
            DEC     R0              ;POINT TO LSB OF ANSWER
            MOV     A,@R0           ;GET LSB OF ANSWER
```

```
            RRC     A                       ;ROTATE RIGHT ONCE
            MOV     @R0,A                   ;SAVE AS LSB OF ANSWER
            DJNZ    R3,DIVBY4               ;LOOP THROUGH 2 TIMES
;
; MULTIPLY "TOTAL SUM" * "SCALE FACTOR COEF"
;
            CALL    XCOEFC                  ;MULTIPLY SUM * SCALE FACTOR
;
; OUTPUT OF THIS STAGE = ABOVE PRODUCT / 256
;
            CALL    STRDAT                  ;CALL ROUTINE TO SAVE R2,R3 AS "DADATA"
;
; SAVE THE RESULTS OF THIS STAGE OF THE FILTER BACK INTO MEMORY
;
            MOV     R1,#DELAY               ;POINT TO SOURCE ADDRESS
            MOV     R0,#STAGE               ;POINT TO STAGE INDICATOR
            MOV     A,@R0                   ;GET STAGE INDICATOR
            RL      A                       ;MULTIPLY POINTER BY 4
            RL      A                       ;BY ROTATING
            ADD     A,R1                    ;ADD TO START OF DESTINATION
            MOV     R1,A                    ;SAVE DESTINATION ADDRESS
            MOV     R0,#NUMBER              ;POINT TO DESTINATION ADDRESS
            CALL    MOVE                    ;MOVE 4 BYTES FROM NUMBER TO DELAY
            MOV     R0,#STAGE               ;POINT TO STAGE INDICATOR
            MOV     A,@R0                   ;GET STAGE INDICATOR
            INC     A                       ;INCREMENT BY 1
            ANL     A,#00000011B            ;LIMIT TO COUNT OF 0 - 3
            MOV     @R0,A                   ;SAVE AS NEW STAGE INDCATOR
            JNZ     FILLOP                  ;IF STAGE INDICATOR > 0 ? JUMP
            MOV     A,R3                    ;GET MSB OF RESULTS
            ANL     A,#11100000B            ;IF ANSWER < MAXIMUM DATA
            JZ      ENDFIL                  ;THEN OK TO SAVE DATA
            MOV     R2,#0F8H                ;ELSE SET DATA =
            MOV     R3,#01FH                ;MAXIMUM ALLOWABLE VALUE
;
; END OF DIGITAL FILTER
;
ENDFIL      CALL    FIXRESP                 ;FIX OUTPUT OF FILTER
            JMP     FILRET                  ;GOTO BACK TO MAIN LOOP
;
; ROUTINE TO DIVIDE R2(LSB) & R3(MSB) BY 8 AND STORE IN "DADATA"
;
FIXRESP     MOV     R7,#03H                 ;SET LOOP COUNTER = 3
            CALL    SHIFT                   ;CALL ROUTINE TO SHIFT R2,R3
STRDAT      MOV     R0,#DADATA+1            ;POINT TO MSB OF D/A DATA
SAVDAT      MOV     A,R3                    ;GET MSB OF ANSWER
            MOV     @R0,A                   ;STORE AS MSB OF DATA
            DEC     R0                      ;POINT TO LSB OF DATA
            MOV     A,R2                    ;GET LSB OF RESULTS
            MOV     @R0,A                   ;STORE AS LSB OF D/A DATA
            RET                             ;RETURN FROM ROUTINE
;
; ROUTINE TO ROTATE R3 THROUGH R2 RIGHT R7 TIMES
;
SHIFT       CLR     C                       ;CLEAR CARRY
            MOV     A,R3                    ;GET MSB OF RESULTS
            RRC     A                       ;ROTATE ONCE RIGHT -> C
            MOV     R3,A                    ;SAVE AS NEW MSB OF RESULTS
            MOV     A,R2                    ;GET LSB OF RESULTS
            RRC     A                       ;ROTATE ONCE RIGHT -> C
            MOV     R2,A                    ;SAVE AS NEW LSB OF RESULTS
            DJNZ    R7,SHIFT                ;LOOP UNTIL R7 = 0
            RET                             ;RETURN
```

```
;
; MOVE 4 CONSECUTIVE BYTE FROM "R0" TO "R1"
;
MOVE    MOV     R7,#4           ;SET LOOP COUNTER TO 4
MOVLOP  MOV     A,@R0           ;GET DATA POINTED TO BY R0
        MOV     @R1,A           ;STORE IN LOCATION POINTED TO BY R1
        INC     R0              ;INCREMENT R0 POINTER - SOURCE
        INC     R1              ;INCREMENT R1 POINTER - DESTINATION
        DJNZ    R7,MOVLOP       ;DECREMENT R7 & LOOP IF > 0
        RET                     ;RETURN FROM ROUTINE
;
; ROUTINE TO SET THE APPROPRAITE THRESHOLD = RESP DATA
;
ADJUST  MOV     A,@R0           ;GET LSB OF SOURCE THRESHOLD
        ADD     A,R4            ;ADD LSB OF DIFFERENCE
        MOV     @R0,A           ;SAVE AS NEW LSB OF THRESHOLD
        INC     R0              ;POINT TO MSB OF SOURCE THRESHOLD
        MOV     A,@R0           ;GET MSB OF SOURCE TRHESHOLD
        ADDC    A,R5            ;ADD MSB OF DIFFERENCE
        MOV     @R0,A           ;SAVE AS NEW MSB OF THRESHOLD
        MOV     R0,#DADATA      ;POINT TO LSB OF FILTERED DATA
        DEC     R1              ;POINT TO LSB OF DEST THRESHOLD
MOVTWO  MOV     A,@R0           ;GET LSB OF FILTERED DATA
        MOV     @R1,A           ;SAVE AS LSB OF THRESHOLD
        INC     R0              ;POINT TO MSB OF FILTERED DATA
        INC     R1              ;POINT TO MSB OF THRESHOLD
        MOV     A,@R0           ;GET MSB OF FILTERED DATA
        MOV     @R1,A           ;SAVE AS MSB OF THRESHOLD
        RET                     ;RETURN
;
; ROUTINE TO FIND DELTA = THE DIFFERENCE / BY THE NUMBER OF INTERRUPTS
;
FDELTA  MOV     A,R7            ;RECALL 3000/LIMITED HR
        SWAP    A               ;SWAP BITS 0-3 & 4-7
        MOV     R6,A            ;SAVE FOR LATTER
        ANL     A,#00001111B    ;MASK IN 4 LSB BITS
        MOV     R7,A            ;SAVE FOR DIVIDE
        MOV     A,R6            ;RECALL SWAPPED 3000/LIMITED HR
        ANL     A,#11110000B    ;MASK IN 4 MSB BITS
        MOV     R6,A            ;SAVE AS LSB OF DIVISOR
        MOV     A,R4            ;GET LSB OF DIFF
        MOV     R2,A            ;SAVE FOR DIVIDE
        MOV     A,R5            ;GET MSB OF DIFF
        MOV     R3,A            ;SAVE FOR DIVIDE
        CALL    DIVIDE          ;DIVIDE DIFF BY # INTERRUPTS
        MOV     A,R7            ;RECALL QUOTIENT
        RET                     ;RETURN
;
; ROUTINE TO ADD TWO 16 BIT NUMBERS TOGETHER RESULTS IN R0
;
TWOADD  MOV     A,@R0           ;GET BYTE 2 OF 32 BIT NUMBER
        ADD     A,@R1           ;ADD TO IT BYTE 1 OF 32 BIT NUMBER
        MOV     @R0,A           ;SAVE AS BYTE 1 OF 32 BIT NUMBER
        INC     R0              ;POINT TO BYTE 2 OF 32 BIT NUMBER
        INC     R1              ;POINT TO BYTE 1 OF 16 BIT NUMBER
        MOV     A,@R0           ;GET BYTE 2 OF 32 BIT NUMBER
        ADDC    A,@R1           ;ADD TO IT BYTE 1 OF 16 BIT NUMBER
        MOV     @R0,A           ;SAVE AS BYTE 2 OF 32 BIT NUMBER
        RET                     ;RETURN
;
; ROUTINE TO DECREASE RESPIRATION THRESHOLDS BY .9675 %
;
```

```
DECTHS  MOV    R5,#0F8H            ;SET LSB OF MULIPILICAND
        MOV    R6,#000H            ;SET MSB OF MULTIPLICAND
;
; ROUTINE TO FIX AUTO & DETECTION THRESHOLDS AFTER INCREASE/DECREASE
;
FIXTHS  MOV    R0,#WINDOW          ;POINT TO WINDOW
        MOV    A,@R0               ;GET WINDOW
        MOV    R4,A                ;SAVE FOR MULTIPLY
        CALL   MULT                ;WINDOW = WINDOW * DECREASE/INCREASE
        MOV    A,R3                ;GET OVERFLOW RESULTS
        JZ     NOTMAX              ;IF RESULTS INDICATE NO OVERFLOW ? JUMP
        MOV    R2,#0FFH            ;ELSE SET RESULTS = 255
NOTMAX  MOV    A,R2                ;GET RESULTS
        ADD    A,#0ECH             ;ADD -20 TO IT
        JC     NOTMIN              ;IF RESULTS >= 20 ? JUMP
        MOV    R2,#014H            ;ELSE SET RESULTS = 20
NOTMIN  MOV    A,R2                ;RECALL ADJUSTED WINDOW RESULTS
        MOV    @R0,A               ;SAVE AS "NEW" WINDOW
        MOV    R0,#NAUTO           ;POINT TO NEG AUTO THRESHOLD
        ADD    A,@R0               ;ADD WINDOW TO NEG AUTO THRESHOLD
        DEC    R0                  ;POINT TO POS AUTO THRESHOLD
        MOV    @R0,A               ;SAVE AS "NEW" POS AUTO THRESHOLD
        MOV    A,R2                ;RECALL "NEW" WINDOW
        MOV    R0,#PTHRES          ;POINT TO LSB OF POS THRESHOLD
        MOV    R1,#NTHRES          ;POINT TO LSB OF NEG THRESHOLD
        ADD    A,@R1               ;ADD "NEW" WINDOW TO LSB NEG THRESHOLD
        MOV    @R0,A               ;SAVE AS LSB OF POS THRESHOLD
        INC    R0                  ;POINT TO MSB OF POS THRESHOLD
        INC    R1                  ;POINT TO MSB OF NEG THRESHOLD
        CLR    A                   ;CLEAR ACCUM
        ADDC   A,@R1               ;ADD WITH CARRY MSB OF NEG THRESHOLD
        MOV    @R0,A               ;SAVE AS MSB OF POS THRESHOLD
        RET                        ;RETURN FROM ADJUSTING THRESHOLDS
;
; TWO (2) - 16 bit COMPARISON ROUTINE
;
; R0 ---> R2,R3 ---> A
; R1 ---> R4,R5 ---> B
; IF A >= B THEN CARRY=1
; IF A < B  THEN CARRY=0
;
COMP2   MOV    A,@R1               ;GET LSB OF "B"
        CPL    A                   ;COMPLEMENT IT
        ADD    A,#01H              ;ADD 1 TO IT FOR 2s COMPLEMENT
        MOV    R4,A                ;SAVE AS LSB OF "B"
        INC    R1                  ;POINT TO MSB OF "B"
        MOV    A,@R1               ;GET MSB OF "B"
        CPL    A                   ;COMPLEMENT IT
        ADDC   A,#00               ;ADD RESULTING CARRY FROM ABOVE
        MOV    R5,A                ;SAVE AS MSB OF "B"
        MOV    A,@R0               ;GET LSB OF "A"
        MOV    R2,A                ;SAVE IN R2
        INC    R0                  ;POINT TO MSB OF "A"
        MOV    A,@R0               ;GET MSB OF "A"
        MOV    R3,A                ;SAVE IN R3
        MOV    A,R2                ;GET LSB OF A
        ADD    A,R4                ;ADD LSB OF -"B"
        MOV    R4,A                ;SAVE RESULTS IN R4
        MOV    A,R3                ;GET MSB OF A
        ADDC   A,R5                ;ADD MSB OF "B" + CARRY FROM ABOVE
        MOV    R5,A                ;SAVE RESULTS IN R5
        ORL    A,R4                ;OR LSB & MSB TOGETHER
        RET                        ;RETURN
```

```
;
;*******************************************
;*      16 BIT by 16 BIT DIVIDE ROUTINE    *
;*                                          *
;* UPON ENTER:                              *
;*    R2 - 8 LSB OF DIVIDEND                *
;*    R3 - 8 MSB OF DIVIDEND                *
;*    R6 - 8 LSB OF DIVISOR                 *
;*    R7 - 8 MSB OF DIVISOR                 *
;* UPON EXIT:                               *
;*    R7 - 8 LSB OF QUOTIENT                *
;*******************************************
;
DIVIDE  MOV     R5,#0           ;CLEAR NEW LSB OF DIVISOR
        MOV     R4,#8           ;SET LOOP COUNTER = 8
DIVLOP  CLR     C               ;CLEAR CARRY
        MOV     A,R7            ;GET MSB OF DIVISOR
        RRC     A               ;ROTATE ONCE RIGHT THROUGH CARRY
        MOV     R7,A            ;SAVE AS NEW MSB
        MOV     A,R6            ;GET XSB OF DIVISOR
        RRC     A               ;ROTATE ONCE RIGHT THROUGH CARRY
        MOV     R6,A            ;SAVE AS NEW XSB
        MOV     A,R5            ;GET LSB OF DIVISOR
        RRC     A               ;ROTATE ONCE RIGHT THROUGH CARRY
        MOV     R5,A            ;SAVE AS NEW LSB
        MOV     A,R7            ;IF MSB OF DIVISOR = 0
        JZ      DIVID           ;THEN START TRUE DIVDIE
        DJNZ    R4,DIVLOP       ;COUNT=COUNT-1 & LOOP
DIVID   MOV     A,R7            ;GET QUOTIENT
        RL      A               ;ROTATE QUOTIENT ONCE TO LEFT
        MOV     R7,A            ;SAVE QUOTIENT
        CLR     C               ;CLEAR CARRY
        MOV     A,R5            ;GET LSB OF "B"
        CPL     A               ;COMPLEMENT IT
        ADD     A,#01           ;ADD 1 TO IT FOR 2s COMPLEMENT
        MOV     R0,A            ;SAVE IN R0
        MOV     A,R6            ;GET MSB OF "B"
        CPL     A               ;COMPLEMENT IT
        ADDC    A,#00           ;ADD RESULTING CARRY FROM ABOVE
        MOV     R1,A            ;SAVE IN R1
        CLR     C               ;CLEAR CARRY AGAIN
        MOV     A,R2            ;GET LSB OF "A"
        ADD     A,R0            ;ADD LSB OF -"B"
        MOV     R0,A            ;SAVE RESULTS IN R0
        MOV     A,R3            ;SET MSB OF "A"
        ADDC    A,R1            ;ADD MSB OF "B" + CARRY FROM ABOVE
        MOV     R1,A            ;SAVE RESULTS IN R1
        ORL     A,R0            ;OR LSB & MSB OF RESULTS TOGETHER
        JNC     DIVJMP          ;IF DIVDIDEND < DIVISOR THEN JUMP
        INC     R7              ;ELSE INCREMENT QUOTIENT BY 1
        MOV     A,R0            ;SAVE DIFFERENCE
        MOV     R2,A            ;AS NEW
        MOV     A,R1            ;DIVIDEND
        MOV     R3,A            ;
DIVJMP  CLR     C               ;CLEAR CARRY
        MOV     A,R6            ;GET MSB OF DIVISOR
        RRC     A               ;ROTATE ONCE TO RIGHT THROUGH CARRY
        MOV     R6,A            ;SAVE AS NEW DIVISOR
        MOV     A,R5            ;GET LSB OF DIVISOR
        RRC     A               ;ROTATE ONCE TO RIGHT THROUGH CARRY
        MOV     R5,A            ;SAVE AS NEW DIVISOR
        DJNZ    R4,DIVID        ;COUNT=COUNT-1 LOOP > 0
        RET                     ;RETURN FROM DIVIDE ROUTINE
```

```
;
; COEFFICIENT LOOK-UP TABLES FOR EACH STAGE OF FILTER
;
COEFA     BYTE      51, 66,100,156
COEFB     BYTE      93,111,149,212
COEFC     BYTE      42, 45, 49, 56
;
; ROUTINE TO SET UP TO MULTIPLY Z-1 BY COEF 'A'
;
XCOEFA    MOV       R0,#COEFA          ;POINT TO COEF 'A' TABLE
          MOV       R1,#NUMBER         ;POINT TO LSB OF Z-1
          JMP       TIMES              ;GOTO MULTIPLY ROUTINE
;
; ROUTINE TO SET UP TO MULTIPLY Z-2 BY COEF 'B'
;
XCOEFB    MOV       R0,#COEFB          ;POINT TO COEF 'B' TABLE
          MOV       R1,#NUMBER+2       ;POINT TO LSB OF Z-2
          JMP       TIMES              ;GOTO MULTIPLY ROUTINE
;
; ROUTINE TO SET UP TO MULTIPLY 'TOTAL SUM' BY COEF 'C'
;
XCOEFC    MOV       R0,#COEFC          ;POINT TO COEF 'C' TABLE
          MOV       R1,#ANSWER         ;POINT TO LSB OF 'TOTAL SUM'
;
;* OBTAIN COEF FOR MULT 'A' AND 16 BIT VALUE FOR MULT 'B' *
;***********************************************************
;
TIMES     MOV       A,R0               ;GET START OF TABLE
          MOV       R0,#STAGE          ;POINT TO STAGE INDICATOR
          ADD       A,@R0              ;ADD STAGE INDICATOR TO START OF TABLE
          MOVP      A,@A               ;GET COEF FOR THIS STAGE
          MOV       R4,A               ;PUT COEF IN R4
          MOV       A,@R1              ;GET LSB OF 16 BIT VALUE
          MOV       R5,A               ;PUT LSB OF 16 BIT VALUE INTO R5
          INC       R1                 ;POINT TO MSB OF 16 BIT VALUE
          MOV       A,@R1              ;GET MSB OF 16 BIT VALUE
          MOV       R6,A               ;PUT MSB OF 16 BIT VALUE INTO R6
;
;***********************************************************
;*                                                         *
;*            8 bit x 16 bit MULTIPLY                      *
;*                                                         *
;===========================================================
;*                                                         *
;* AT ENTRY:                                               *
;*    R4 = 8 BIT VALUE                         'A'         *
;*    R5 = 8 LSB OF 16 BIT VALUE               'B'         *
;*    R6 = 8 MSB OF 16 BIT VALUE               'B'         *
;*                                                         *
;*    AT EXIT:                                             *
;*    R1 = 8 LSB OF 32 BIT ANSWER        'PRODUCT'         *
;*    R2 = 8 XSB OF 32 BIT ANSWER        'PRODUCT'         *
;*    R3 = 8 MSB OF 32 BIT ANSWER        'PRODUCT'         *
;*                                                         *
;*REGISTERS EFFECTED: A,R1,R2,R3,R4,R5,R6,R7               *
;*                                                         *
;***********************************************************
;
MULT      CLR       A                  ;CLEAR ANSWER BITS
          MOV       R1,A               ; 8 LSB OF ANSWER
          MOV       R2,A               ; 8 XSB OF ANSWER
          MOV       R3,A               ; 8 MSB OF ANSWER
          MOV       R7,A               ; 8 MSB OF 16 BIT VALUE 'B'
```

```
        MOV     A,R4            ;GET MULTIPLICAND
MLOOP   JZ      MULRET          ;JUMP TO RETURN IF = ZERO
        JB0     PATHA           ;ELSE IF BIT(0) = 1 ? ADD "B" TO ANSWER
        JMP     PATHB           ;IF NOT DOUBLE "B"
PATHA   MOV     A,R1            ;PRODUCT = PRODUCT + "B"
        ADD     A,R5            ;ADD LSB OF "B"
        MOV     R1,A            ;STORE IN ANSWER
        MOV     A,R2            ;GET XSB OF ANSWER
        ADDC    A,R6            ;ADD MSB OF "B"
        MOV     R2,A            ;STORE IN ANSWER
        MOV     A,R3            ;GET MSB OF "B"
        ADDC    A,R7            ;ADD MSB OF "B"
        MOV     R3,A            ;STORE IN ANSWER
PATHB   CLR     C               ;"B" = "B" * 2
        MOV     A,R5            ;GET LSB OF "B"
        RLC     A               ;ROTATE ONCE LEFT --> CARRY
        MOV     R5,A            ;STORE AS NEW LSB
        MOV     A,R6            ;GET XSB OF "B"
        RLC     A               ;ROTATE ONCE LEFT --> CARRY
        MOV     R6,A            ;STORE AS NEW XSB
        MOV     A,R7            ;GET MSB OF "B"
        RLC     A               ;ROTATE ONCE LEFT --> CARRY
        MOV     R7,A            ;STORE AS NEW MSB
        CLR     C               ;CLEAR CARRY
        MOV     A,R4            ;GET LSB OF "A"
        RRC     A               ;ROTATE ONCE RIGHT --> CARRY
        MOV     R4,A            ;STORE AS NEW "A"
        JMP     MLOOP           ;COUNT=COUNT-1 & LOOP > 0
;
MULRET  RET                     ;RETURN FROM MULTIPLY ROUTINE
;
; ROUTINT TO GET RESPIRATION SAMPLE INTERVAL USING PRESENT B-B HR
;
SAMINT  CLR     A               ;CLEAR ACCUM
        MOV     R0,#CRT0        ;POINT TO TO COMMAND REGISTER
        MOVX    @R0,A           ;STOP & RESET TIMER 0
        MOV     R2,#00000101B   ;SET COMMAND MODE TO SQUARE WAVE *1
        MOV     R1,#SAMPLE      ;POINT TO CURRENT B-B HEART RATE
        MOV     A,@R1           ;GET LIMITED HEART RATE
        ADD     A,#0C4H         ;ADD -60 TO IT
        MOV     R3,A            ;SAVE LIMITED HEART RATE -60
        JC      GRT60           ;IF HEART RATE < 60 ? JUMP
        MOV     R2,#00001101B   ;SET COMMAND MODE TO SQUARE WAVE *2
        MOV     A,@R1           ;RECALL ORIGINAL LIMITED HR
        ADD     A,#0E2H         ;ADD -30 TO IT
        RL      A               ;DOUBLE IT
        MOV     R3,A            ;SAVE FOR LATTER (HR-30)*2
GRT60   MOV     A,R2            ;GET COMMAND MODE
        MOVX    @R0,A           ;RE-STORE COMMAND
        MOV     A,R3            ;RECALL LIMITED HR-30
        RL      A               ;DOUBLE IT
        INC     A               ;AND ADD 1 TO IT (HR*2)+1
        MOV     R2,A            ;SAVE FOR LATTER
        CALL    RSPCNT          ;GET LSB OF SAMPLE FROM TABLE
        MOV     R1,#LSBT0       ;POINT TO LSB OF TIMER 0
        MOVX    @R0,A           ;OUTPUT TO LSB OF TIMER 0
        INC     R1              ;POINT TO MSB OF TIME 0
        DEC     R2              ;DECREMENT COUNT; COUNT = HR * 2
        MOV     A,R2            ;GET COUNT (HR*2)
        CALL    RSPCNT          ;GET MSB OF SAMPLE FROM TABLE
        MOVX    @R0,A           ;OUTPUT TO MSB OF TIMER 0
        MOV     R0,#START0      ;POINT TO TIMER 0 START ADDRESS
        MOVX    @R0,A           ;RE-START TIMER 0
```

```
            RET                              ;RETURN
;
;*****************************************
;* RESPIRATION SAMPLE LOOK-UP TABLE ROUTINE *
;*****************************************
;
GROUPA  WORD    40000,39344,38710,38095,37500,36923,36364,35821,35294,34783
GROUPB  WORD    34286,33803,33333,32877,32432,32000,31579,31169,30769,30380
GROUPC  WORD    30000,29630,29268,28916,28571,28235,27907,27586,27273,26966
GROUPD  WORD    26667,26374,26087,25806,25532,25263,25000,24742,24490,24242
GROUPE  WORD    24000,23762,23529,23301,23077,22857,22642,22430,22222,22018
GROUPF  WORD    21818,21622,21429,21239,21053,20870,20690,20513,20339,20168
GROUPG  WORD    20000,19835,19672,19512,19355,19200,19048,18898,18750,18605
GROUPH  WORD    18462,18321,18182,18045,17910,17778,17647,17518,17391,17266
GROUPI  WORD    17143,17021,16901,16783,16667,16552,16438,16327,16216,16107
GROUPJ  WORD    16000,15894,15789,15686,15584,15484,15385,15287,15190,15094
GROUPK  WORD    15000,14907,14815,14724,14634,14545,14458,14371,14286,14201
GROUPL  WORD    14118,14035,13953,13873,13793,13714,13636,13559,13483,13408
GROUPM  WORD    13333
;
RSPCNT  MOVP    A,@A                    ;USING ACCUM, GET BYTE FROM TABLE
        RET                             ;RETURN
;
; ROUTINE TO ADD A 32 BIT NUMBER WITH A 16 BIT NUMBER
;
Z1ADD   MOV     R1,#NUMBER              ;POINT TO LSB OF Z-1
Z2ADD   MOV     R0,#ANSWER              ;POINT TO LSB OF ANSWER
DADD    CALL    TWOADD                  ;ADD R0 & R1 TOGETHER
        INC     R0                      ;POINT TO BYTE 2 OF 32 BIT NUMBER
        CLR     A                       ;CLEAR ACCUM
        ADDC    A,@R0                   ;ADD CARRY TO BYTE 2 OF 32 BIT NUMBER
        MOV     @R0,A                   ;SAVE AS BYTE 2 OF 32 BIT NUMBER
        RET                             ;RETURN FROM DOUBLE ADD
        NOP
;
        END
!!
;
        NAME    INTRPT
;
;************************
;* VARIABLE DEFINITION *
;************************
;
AVGCNT  EQU     022H
INSTAT  EQU     023H
STATUS  EQU     024H
TSTAT   EQU     025H
TSTCNT  EQU     026H
FLASH   EQU     027H
ATIMER  EQU     02AH
APMAX   EQU     02CH
BBINT   EQU     02DH
DECAY   EQU     02FH
HRLED   EQU     030H
RRINT   EQU     032H
HRDA    EQU     034H
OLDHR   EQU     036H
DELTA   EQU     03AH
NEWCVA  EQU     03CH
OLDCVA  EQU     03EH
RBRCNT  EQU     041H
SQUARE  EQU     042H
```

```
        LEDCNT  EQU     044H
        SILCNT  EQU     045H
        AUDCNT  EQU     047H
        INTCNT  EQU     049H
        UPSTAT  EQU     04AH
        ACCUM   EQU     05BH
        PSWORD  EQU     05CH
        PORTA   EQU     0C0H
        PORTB   EQU     0C1H
        PORTC   EQU     0C2H
        CLEARA  EQU     0C8H
        SETA    EQU     0CCH
;
;*****************************
;* DECLARE ROUTINE NAMES *
;*****************************
;
        GLOBAL  INT
        GLOBAL  SAMHLD
        GLOBAL  DIVIDE
        GLOBAL  ALRMTST
        GLOBAL  SAVEHR
        GLOBAL  INCSEC
        GLOBAL  COMP2
        GLOBAL  MOVTWO
        GLOBAL  TWOADD
        GLOBAL  CLRTWO
        GLOBAL  OUTDA
        GLOBAL  FSHLED
        GLOBAL  ROLEFT
        GLOBAL  SHIFT
;
; DECLARATION OF MODULE SAPCE ALLOCATION
;
        SECTION INTRPT,ABSOLUTE
        ORG     1EBH
;
; 500 Hz INTERRUPT: 1st SAVE REGISTER & STATUS
;
INT     MOV     R0,#ACCUM       ;POINT TO TEMP ACCUM
        MOV     @R0,A           ;SAVE ACCUM IN RAM
;
; SEE IF MONITOR IS IN SELF TEST, THEN OUTPUT .5 Hz RAMP WAVEFORM
;
        MOV     R0,#OLDCVA+1    ;POINT TO MSB OF OLD CVA DATA
        JF1     TSTOUT          ;IF IN TEST ? JUMP
        JMP     UPCVA           ;ELSE GOTO UPDATE CVA OUTPUT
;
; IF MONITOR IS IN SELF TEST, THEN OUTPUT .5 HZ RAMP WAVEFORM.
;
TSTOUT  DEC     R0              ;POINT TO LSB OF OLD CVA DATA
        MOV     A,@R0           ;GET LSB OF OLD CVA DATA
        ADD     A,#01000000B    ;ADD 1 D/A LSB TO OLD CVA DATA
        MOV     @R0,A           ;ADD TO LSB OF OLD CVA DATA
        INC     R0              ;POINT TO MSB OF OLD CVA DATA
        JNC     JMPOUT          ;IF LSB > 0 ? JUMP
        INC     @R0             ;ELSE INCREMENT MSB OF DATA
JMPOUT  JMP     OUTCVA          ;GOTO OUTPUT OLD CVA DATA
;
; ADD DELTA CVA DIFFERENCE TO OLD CVA DATA
;
UPCVA   MOV     R1,#UPSTAT      ;POINT TO UPDATE STATUS
        MOV     A,@R1           ;GET CURRENT UPDATE STATUS
```

```
            JB7     OUTCVA              ;IF UPDATING CVA DATA ? JUMP
            DEC     R0                  ;POINT TO LSB OF OLD CVA DATA
            MOV     R1,#DELTA           ;POINT TO LSB OF DELTA DIFF
            CALL    TWOADD              ;ADD DELTA TO OLD CVA DATA
            MOV     A,@R1               ;GET SIGN OF DELTA
            MOV     R7,A                ;SAVE FOR LATTER
            INC     R1                  ;POINT TO LSB OF NEW CVA DATA
            DEC     R0                  ;POINT TO LSB OF OLD CVA DATA
            JB7     NOTOVR              ;IF SIGN NEGATIVE ? JUMP
            CPL     C                   ;ELSE COMPLEMENT CARRY
NOTOVR      JNC     EQUAL               ;IF NEG/NO CARRY OR POS/CARRY ? JUMP
            CALL    COMP2               ;COMPARE THE NEW vs OLD CVA DATA
            MOV     A,R7                ;RECALL SIGN OF DELTA DIFF
            CPL     A                   ;COMPLEMENT SIGN OF DELTA
            JB7     POSDEL              ;IF SIGN POSITIVE ? THEN JUMP
            CPL     C                   ;COMPLEMENT CARRY CHECK AS POS
POSDEL      JNC     OUTCVA              ;IF OLD DID NOT 'GO PAST' NEW ? JUMP
EQUAL       MOV     R0,#NEWCVA          ;POINT TO LSB OF NEW CVA DATA
            MOV     R1,#OLDCVA          ;POINT TO LSB OF OLD CVA DATA
            CALL    MOVTWO              ;SET OLD CVA = NEW CVA
;
; OUTPUT OLD CVA DATA TO D/A
;
OUTCVA      CALL    OUTDA               ;OUTPUT CVA DATA VALUE IN D/A
;
; ENABLE "FILTERED RESPIRATION" DG211 CHANNEL 2
;
            ORL     P2,#10000000B       ;TURN ON "FILTERED RESPIRATION" OUTPUT
            CALL    SAMHLD              ;ENABLE OUTPUT FOR 50 uSEC
;
; OUTPUT "BEAT-to-BEAT HEART RATE" TO D/A
;
            INC     R0                  ;POINT TO MSB OF OLD CVA DATA
            JF1     OUTRAMP             ;IF IN SELF TEST ? JUMP
            MOV     R0,#HRDA            ;POINT TO LSB OF HR OUTPUT
            MOV     R1,#OLDHR           ;POINT TO LSB OF OLD HR OUTPUT
            CALL    COMP2               ;COMPARE THE HR OUTPUTS
            JZ      OUTRAMP             ;IF OLD = NEW OUTPUT ? JUMP
            RLC     A                   ;ROTATE IN CARRY
            MOV     R6,A                ;SAVE FOR LATTER
            MOV     A,R4                ;GET LSB OF DIFFERENCE
            MOV     R2,A                ;SAVE FOR SHIFT
            MOV     A,R5                ;GET MSB OF DIFFERENCE
            MOV     R3,A                ;SAVE FOR SHIFT
            MOV     R7,#004H            ;SET LOOP COUNTER = 4
            CALL    SHIFT               ;DIVIDE DIFF BY 16
            MOV     A,R6                ;RECALL CARRY FLAG
            JB0     PHRDIF              ;IF ORIGINAL DIFF WAS POSITIVE ? JUMP
NHRDIF      MOV     A,R3                ;GET MSB OF DIFFERENCE
            ORL     A,#11110000B        ;"OR" IN -1 FOR MSB
            MOV     R3,A                ;SAVE AS MSB OF DIFF
            JMP     ADDIFF              ;GOTO ADD DIFF/16
PHRDIF      MOV     A,R2                ;GET LSB OF DIFF/16
            ORL     A,#00000001B        ;MAKE LSB OF DIFF/16 ATLEAST 1
            MOV     R2,A                ;SAVE AS LSB OF DIFF/16
ADDIFF      MOV     R0,#OLDHR           ;POINT TO LSB OF OLD HR OUTPUT
            MOV     A,@R0               ;GET LSB OF OLD HR OUTPUT
            ADD     A,R2                ;ADD DIFF TO LSB OF OLD HR OUTPUT
            MOV     @R0,A               ;SAVE AS LSB OF OLD HR OUTPUT
            INC     R0                  ;POINT TO MSB OF OLD HR OUTPUT
            MOV     A,@R0               ;GET MSB OF OLD HR OUTPUT
            ADDC    A,R3                ;ADD CARRY TO MSB OF OLD HR OUTPUT
            MOV     @R0,A               ;SAVE AS MSB OF OLD HR OUTPUT
```

```
OUTRAMP  CALL     OUTDA              ;CALL ROUTINE TO OUTPUT TO D/A
;
; ENABLE "BEAT-to-BEAT HEART RATE" OUTPUT DG211 CHANNEL 3
;
         ORL      P2,#11000000B      ;TURN ON "BEAT-BEAT HR" OUTPUT
         CALL     SAMHLD             ;ENABLE OUTPUT FOR 50 uSEC
;
; RECALL PORT B INPUT STATUS AND TEST FOR LEADS OFF
;
         JB6      NOLOSE             ;IF LEADS ON ? JUMP
;
; INDICATE LEADS OFF CONDITION
;
         MOV      R1,#INSTAT         ;POINT TO CURRENT INTERRUPT STATUS
         MOV      A,@R1              ;GET CURRENT STATUS
         ANL      A,#01101001B       ;CLEAR BRADY,TACHY & APNEA ALARMS
         MOV      @R1,A              ;SAVE AS NEW STATUS
         MOV      R0,#TSTCNT         ;POINT TO TEST STATUS COUNTER
         MOV      R2,#01BH           ;SET LOOP COUNTER = 27
         CLR      A                  ;CLEAR ACCUM
CLRLOP   MOV      @R0,A              ;CLEAR NEXT BYTE OF RAM
         INC      R0                 ;POINT TO NEXT BYTE OF RAM
         DJNZ     R2,CLRLOP          ;LOOP THROUGH 24 BYTES
         MOV      @R0,#09CH          ;SET BASE LINE COUNTER = 100mSEC
         CPL      F1                 ;COMPLEMENT SELF TEST INDICATOR
         JF1      CLTIND             ;IF WAS NOT IN SELF TEST ? JUMP
         ANL      P1,#10000000B      ;CLEAR ALL LEDS
CLTIND   CLR      F1                 ;CLEAR SELF TEST INDICATOR
         ORL      P1,#00100000B      ;SET LEADS OFF INDICATOR
         JMP      UPDATE             ;ELSE GOTO TO UPDATE 20 mSEC COUNT
;
; LEADS ON, INCREMENT R-R INTERVAL BY 1, IF COUNT < 750 COUNTS
;
NOLOSE   CPL      F0                 ;INDICATE LEADS ON
         MOV      R1,#RRINT+1        ;POINT MSB OF TO R-R INTERVAL
         MOV      A,@R1              ;GET MSB OF R-R INTERVAL
         ADD      A,#0FDH            ;ADD -3 TO MSB OF R-R INTERVAL
         DEC      R1                 ;POINT TO LSB OF R-R INTERVAL
         JNC      INCRINT            ;IF R-R INTERVAL < 767 ? JUMP
         MOV      A,@R1              ;GET LSB OF R-R INTERVAL
         ADDC     A,#018H            ;ADD LSB OF -1000 TO R-R INTERVAL
         JNC      INCRINT            ;IF R-R INTERVAL < 1000 ? THEN JUMP
         MOV      R7,#1EH            ;SET R7 = 30
         CALL     SAVEHR             ;SET HR=30 AND GET RESP SAMPLE
         JMP      QRSTST             ;GOTO TEST FOR QRS
INCRINT  INC      @R1                ;INCREMENT LSB OF INTERVAL
         MOV      A,@R1              ;GET LSB OF R-R INTERVAL
         JNZ      QRSTST             ;IF LSB OF R-R INTERVAL = 0 ? JUMP
         INC      R1                 ;ELSE POINT TO MSB OF R-R INTERVAL
         INC      @R1                ;INCREMENT MSB OF R-R INTERVAL
         DEC      R1                 ;POINT TO LSB OF R-R INTERVAL
;
; WAIT .24 SECONDS AFTER ANY HEART BEAT TO TEST FOR QRS HIGH/LOW
;
QRSTST   MOV      A,@R1              ;RECALL LSB OF R-R INTERVAL
         MOV      R6,A               ;SAVE FOR LATTER
         ADD      A,#088H            ;ADD LSB OF -120 TO R-R INTERVAL
         INC      R1                 ;POINT TO MSB OF R-R INTERVAL
         MOV      A,@R1              ;GET MSB OF R-R INTERVAL
         MOV      R7,A               ;SAVE FOR LATTER
         ADDC     A,#0FFH            ;ADD MSB OF -120 TO R-R INTERVAL
         JNC      UPDATE             ;IF INTERVAL < .24 SEC ? JUMP AROUND
;
```

```
; IF QRS INPUT IS HIGH ? THEN GOTO INDICATE HEART BEAT
;
        MOV     R0,#INSTAT      ;POINT TO CURRENT INTERRUPT STATUS
        MOV     A,R5            ;RECALL PORT B INPUT STATUS
        JB7     QRSHIGH         ;IF QRS HIGH ? THEN JUMP
;
; IF QRS IS LOW, SET UP FOR NEXT RISING EDGE
;
QRSLOW  MOV     A,@R0           ;GET CURRENT STATUS
        ANL     A,#01111111B    ;CLEAR QRS FOUND STATUS
        MOV     @R0,A           ;STORE AS NEW STATUS
        JMP     UPDATE          ;GOTO UPDATE 20 mSec COUNTER
;
; IF QRS IS HIGH, SEE IF IT IS THE FIRST TIME AND INDICATE A BEAT
;
QRSHIGH MOV     A,@R0           ;GET CURRENT STATUS
        JB7     UPDATE          ;IF ALREADY FOUND QRS ? JUMP
        MOV     A,@R0           ;RECALL CURRENT STATUS
        ORL     A,#11000000B    ;INDICATE FOUND QRS
        MOV     @R0,A           ;SAVE AS NEW STATUS
        MOV     R0,#HRLED       ;POINT TO HEART BEAT LED COUNTER
        MOV     @R0,#0FBH       ;SET COUNTER = -5 (100 mSEC)
        MOV     R0,#RRINT       ;POINT TO LSB OF R-R INTERVAL
        CALL    CLRTWO          ;CLEAR R-R INTERVAL
        MOV     R2,#030H        ;SET DIVIDEND = 30000
        MOV     R3,#075H        ;
        CALL    DIVIDE          ;DIVIDE 30000 BY R-R INTERVAL
        CALL    SAVEHR          ;SAVE B-B HR AND GET RESP SAMPLE
;
; UPDATE 20 mSec INTERRUPT COUNTER
;
UPDATE  MOV     R0,#INTCNT      ;POINT TO INTERRUPT COUNTER
        INC     @R0             ;INCREMENT COUNT BY 1
        MOV     R1,#INSTAT      ;POINT TO INTERRUPT STATUS
        MOV     A,@R1           ;GET INTERRUPT STATUS
        JB6     CLBEAT          ;IF BEAT JUST OCCURRED ? JUMP
        MOV     A,@R0           ;RECALL INTERRUPT COUNTER
        ADD     A,#0F6H         ;ADD -10 TO IT
        JC      NOT20           ;IF COUNT WAS >= 10 ? JUMP
        MOV     @R0,A           ;ELSE SAVE REMAINDER
        JMP     INREST          ;GOTO 20 mSEC ROUTINE
CLBEAT  ANL     A,#10111111B    ;CLEAR BIT FOR BEAT JUST OCCURRED
        MOV     @R1,A           ;SAVE AS NEW INTERRUPT STATUS STATUS
NOT20   JMP     SQRTST          ;JUMP TO OUTPUT 2 Hz SQUARE WAVE
;
; INPUT RESET BUTTON STATUS AND SAVE
;
INREST  MOV     R0,#PORTC       ;POINT TO PORT C INPUT STATUS
        MOVX    A,@R0           ;INPUT PORT C STATUS
        ANL     A,#00001000B    ;MASK IN RESET BUTTON STATUS
        MOV     R7,A            ;SAVE FOR LATTER
;
; SEE IF RESET BUTTON PRESSED OR SILENCE COUNTER IN PROGRESS ?
;
        MOV     R0,#SILCNT+1    ;POINT TO MSB OF SILENCE COUNTER
        MOV     A,@R0           ;GET MSB OF SILENCE COUNTER
        JNZ     SILON           ;IF COUNTER ALREADY STARTED ? JUMP
        JF0     JMPLED          ;IF LEADS ARE ON ? JUMP
        MOV     A,R7            ;RECALL RESET BUTTON STATUS
        JNZ     CLRALM          ;IF RESET BUTTON PRESSED ? JUMP
;
; IF NEITHER AND LEADS OFF PRESENT ? DELAY AUDIO ALARM FOR 2 SEC
;
```

```
LEDLAY   MOV    R0,#LEDCNT        ;POINT TO LEADS OFF COUNTER
         MOV    A,@R0             ;GET LEADS OFF COUNTER
         ADD    A,#09CH           ;ADD -100 TO IT
         JZ     SETLSD            ;IF COUNT = 100 ? JUMP
         INC    @R0               ;INCREMENT LEADS OFF COUNTER
JMPLED   JMP    LEDTST            ;GOTO SELF TEST CHECK
SETLSD   MOV    A,@R1             ;RECALL CURRENT STATUS
         ORL    A,#00100000B      ;SET LEADS OFF
         MOV    @R1,A             ;SAVE AS NEW STATUS
         JMP    LEDTST            ;GO TO LEAD TEST
;
; CONTINUE SILENCE COUNTER FOR 30 SECONDS, ONCE STARTED
;
CLRALM   ANL    P1,#11101001B     ;CLEAR HR & APNEA LEDS
SILON    MOV    R0,#SILCNT        ;POINT TO LSB OF SILENCE COUNTER
         CALL   INCSEC            ;UPDATE SILENCE COUNTER BY 20 mSec
         MOV    A,@R0             ;RECALL SILENCE COUNTER
         MOV    A,@R1             ;ELSE RECALL CURRENT INTERRUPT STATUS
         ANL    A,#11011111B      ;CLEAR LEADS OFF ALARM BIT
         MOV    @R1,A             ;SAVE AS NEW STATUS
         MOV    A,@R0             ;RECALL SILENCE COUNTER
         ADD    A,#0E3H           ;ADD -29 TO IT
         JNZ    LEDTST            ;IF COUNT <> 29 SEC ? JUMP
         MOV    @R0,A             ;CLEAR SILENCE COUNTER
         MOV    A,@R1             ;RECALL CURRENT INTERRUPT STATUS
         ORL    A,#00100000B      ;ENABLE LEADS OFF ALARM BIT
         MOV    @R1,A             ;SAVE AS NEW INTERRUPT STATUS
;
; TEST FOR LEADS OFF AGAIN
;
LEDTST   JF0    LEDSON            ;IF LEADS ON FLAG SET ? THEN JUMP
         JMP    BATEST            ;ELSE GOTO BATTERY TEST ROUTINE
;
; INDICATE LEADS ARE ON
;
LEDSON   MOV    R0,#LEDCNT        ;POINT TO LEADS OFF COUNTER
         MOV    @R0,#00H          ;SET LEADS OFF COUNTER = 0
         MOV    A,@R1             ;RECALL CURRENT INTERRUPT STATUS
         ANL    A,#11011111B      ;CLEAR LEADS OFF INDICATOR
         MOV    @R1,A             ;SAVE AS NEW STATUS
;
; TEST TO INCREMENT BREATH-to-BREATH APNEA INTERVAL COUNTER
;
         MOV    R0,#APMAX         ;POINT TO MAXIMUM APNEA COUNT
         MOV    A,@R0             ;GET MAXIMUM APNEA COUNT
         MOV    R2,A              ;SAVE FOR LATTER
         DEC    R0                ;POINT TO MSB OF APNEA TIMER
         CPL    A                 ;COMPLEMENT MAX APNEA COUNT
         INC    A                 ;AND ADD 1 TO IT
         ADD    A,@R0             ;ADD MSB OF APNEA TIMER
         JNC    INCAT             ;IF APNEA TIMER < MAX COUNT ? JUMP
         MOV    A,R2              ;RECALL MAXIMUM APNEA COUNT
         MOV    @R0,A             ;SET MSB OF APNEA TIMER = MAX COUNT
         CLR    A                 ;CLEAR ACCUM
         DEC    R0                ;POINT TO LSB OF APNEA TIMER
         MOV    @R0,A             ;SET LSB OF APNEA TIMER = 0
         JMP    INCBT             ;GOTO INCREMENT BR-BR INTERVAL
INCAT    DEC    R0                ;POINT TO LSB OF APNEA TIMER
         CALL   INCSEC            ;UPDATE APNEA TIMER IN 1 SEC INTERVALS
;
; INCREMENT BREATH-to-BREATH INTERVAL BY 1 - 20 mSec COUNT
;
INCBT    MOV    R1,#BRINT         ;POINT TO BR-BR INTERVAL COUNTER
```

```
           MOV      A,@R1              ;GET MSB OF BR-BR INTERVAL
           CPL      A                  ;COMPLEMENT IT
           JZ       WEIGHT             ;IF BR-BR INTERVAL = 5.1 SEC ? JUMP
           INC      @R1                ;ELSE INCRMENT BR-BR INTERVAL BY 1
;
; DETERMINE IF A BREATH OCCURED IN THE LAST 20 mSEC ?
;
WEIGHT     INC      R1                 ;POINT TO BREATH STATUS INDICATOR
           MOV      A,@R1              ;GET BREATH STATUS INDICATOR
           JZ       UPAVG              ;IF NO BREATH OCCURRED ? JUMP
           CLR      A                  ;ELSE CLEAR ACCUM
           MOV      @R1,A              ;CLEAR BREATH STATUS INDICATOR
           DEC      R1                 ;POINT TO BR-BR INTERVAL COUNTER
;
; IF APNEA TIMER < 5 SECONDS ? THEN CLEAR APNEA TIMER.
;
           MOV      R0,#ATIMER+1       ;POINT TO MSB OF APNEA TIMER
           MOV      A,@R0              ;RECALL MSB OF APNEA TIMER
           ADD      A,#0FBH            ;ADD -5 TO MSB OF APNEA TIMER
           JNC      CLRAPT             ;IF MSB OF APNEA TIMER < 5 ? JUMP
           MOV      @R0,A              ;SAVE MSB-5 OF APNEA TIMER
;
; IF LAST BREATH-BREATH INTERVAL < 5 SEC ? THEN CLEAR APNEA TIMER
;
           MOV      A,@R1              ;GET BR-BR INTERVAL COUNT
           ADD      A,#006H            ;ADD - 250 TO IT
           JC       CLRBINT            ;IF BR-BR INTERVAL > 5 SEC ? JUMP
CLRAPT     DEC      R0                 ;POINT TO LSB OF APNEA TIMER
           CALL     CLRTWO             ;ELSE CLEAR APNEA TIMER
CLRBINT    MOV      @R1,#000H          ;CLEAR BR-BR INTERVAL COUNTER
;
; UPDATE HEART RATE AVERAGE EVERY .12 SEC
;
UPAVG      MOV      R0,#AVGCNT         ;POINT TO HR AVERAGE UPDATE COUNTER
           INC      @R0                ;INCREMENT COUNT BY 1
           MOV      A,@R0              ;GET UPDATE COUNTER
           ADD      A,#0FAH            ;ADD -6 TO IT
           JNZ      SLFTST             ;IF COUNT < 6 ? THEN JUMP AROUND
           MOV      @R0,A              ;ELSE CLEAR UPDATE COUNTER
           DEC      R0                 ;POINT TO CURRENT AVG HEART RATE
           MOV      A,@R0              ;GET CURRENT AVG HEART RATE
           DEC      R0                 ;POINT TO B-B HEART RATE
           CPL      A                  ;COMPLEMENT CURRENT AVG HEART RATE
           INC      A                  ;AND ADD 1 TO IT
           ADD      A,@R0              ;ADD TO B-B HEART RATE
           INC      R0                 ;POINT TO AVG HEART RATE
           JZ       SLFTST             ;IF AVG = B-B ? THEN JUMP
           SWAP     A                  ;ROTATE RIGHT 4 TIMES (DIVIDE BY 8)
           RL       A                  ;ROTATE LEFT 1 TIMES (MULTIPLY BY 2)
           JC       POSDIF             ;IF AVG < B-B ? THEN JUMP TO POS DIFF
           ORL      A,#11100000B       ;MASK IN 3 MSB BITS
           JMP      FIXAVG             ;GOTO ADD DIFF TO B-B HEART RATE
POSDIF     ANL      A,#00011111B       ;MASK OUT 3 LSB BITS
           INC      A                  ;AND ADD 1 TO IT
FIXAVG     ADD      A,@R0              ;ADD DIFF/8 TO AVG HEART RATE
           MOV      @R0,A              ;SAVE AS AVG HEART RATE
;
; TEST TO SEE IF HR = 120 BPM, BR = 60 BrPM AND SIZE = 1 ohm ?
;
SLFTST     MOV      R1,#TSTAT          ;POINT TO SELF TEST STATUS
           MOV      A,@R1              ;GET SELF TEST STATUS
           CPL      A                  ;COMPLEMENT PASS/FAIL BITS
```

```
           ANL       A,#00001111B       ;MASK IN ALL SELF TEST INDICATORS
           JNZ       NOTEST             ;IF BOTH INDICATORS NOT SET ? JUMP
           JF1       FSHTST             ;IF ALREADY IN SELF TEST ? JUMP
           INC       R1                 ;ELSE POINT TO SELF TEST COUNTER
           INC       @R1                ;INCREMENT SELF TEST COUNTER BY 1
           MOV       A,@R1              ;GET SELF TEST COUNTER
           JNZ       CHKRST             ;IF SELF TEST COUNTER < 5.12 SEC ? JUMP
           INC       R1                 ;POINT TO FLASH COUNTER
           MOV       @R1,A              ;SET FLASH COUNTER = 0
           INC       A                  ;SET LSB OF ACCUM
           OUTL      P1,A               ;OUTPUT 1ST LED
           CPL       F1                 ;INDICATE IN SELF TEST
           MOV       R0,#CLEARA         ;POINT TO CLEAR BIT IN PORT A
           MOV       A,#00001000B       ;SET REAR PANEL ALARM INDICATOR
           MOVX      @R0,A              ;CLEAR REAR PANEL ALARM
;
; IF IN SELF TEST FOR 5.12 SEC ? FLASH LEDS CONTINIOUSLY EVERY 200 mSec
;
FSHTST     MOV       R1,#FLASH          ;POINT TO FLASH COUNTER
           INC       @R1                ;INCREMENT FLASH COUNTER BY 1
           MOV       A,@R1              ;GET FLASH COUNTER
           ADD       A,#0F6H            ;ADD - 10 TO IT
           JNZ       ENDFSH             ;IF SELF TEST COUNTER < 10 ? JUMP
           MOV       @R1,A              ;ELSE RESET COUNTER TO 0
           CALL      FSHLED             ;FLASH NEXT LED
ENDFSH     JMP       DECTST             ;GOTO INCREMENT DECAY COUNTER
;
; IF NOT IN SELF TEST ? CLEAR SELF TEST STATUS AND COUNTERS
;
NOTEST     JF1       CSLFST             ;IF MONITOR WAS IN SELF TEST ? JUMP
           JMP       CLRFSH             ;IF NOT IN SELF TEST ? JUMP
CSLFST     ANL       P1,#10000000B      ;ELSE CLEAR ALL 7 LEDS
CLRFSH     CLR       F1                 ;CLEAR SELF TEST INDICATOR
           INC       R1                 ;POINT TO SELF TEST COUNTER
           CLR       A                  ;CLEAR ACCUM
           MOV       @R1,A              ;CLEAR SELF TEST COUNTER
;
; CHECK TO SEE IF RESET BUTTON HAS BEEN PRESSED ?
;
CHKRST     MOV       A,R7               ;RECALL RESET BUTTON STATUS
           JZ        CHKALM             ;IF NOT PRESSED ? JUMP
           MOV       R1,#INSTAT         ;POINT TO CURRENT ALARM STATUS
           MOV       A,@R1              ;RECALL CURRENT ALARM STATUS
           ANL       A,#00110110B       ;MASK IN ONLY ALARM BITS
           MOV       R2,A               ;SAVE FOR LATTER
           IN        A,P1               ;INPUT LED STATUS
           ANL       A,#11001001B       ;MASK OUT ALARM LEDS
           ORL       A,R2               ;OR IN CURRENT ALARM STATUS
           OUTL      P1,A               ;OUTPUT NEXT CURRENT LED STATUS
;
; CHECK FOR APNEA, BRADYCARDIA AND TACHYCARDIA ALARMS
;
CHKALM     CALL      ALRMTST            ;TEST HR vs. BRADY & TACHY LIMITS
;
; INPUT LINE POWER STATUS AND CHECK FOR LOW BATTERY
;
BATEST     IN        A,P2               ;INPUT BATTERY STATUS BITS
           JB4       CHKLOW             ;IF NO LINE POWER ? JUMP
BATOFF     ANL       P1,#10111111B      ;TURN OFF LOW BATTERY ALARM
           MOV       R7,#000H           ;SET AUDIO COUNT LIMIT = 0 SEC
           JMP       AUDIO              ;GOTO TURN ON AUDIO FOR BABY ALARMS
CHKLOW     JB5       BATOFF             ;IF NOT LOW BATTERY ? JUMP
           ORL       P1,#01000000B      ;TURN ON LOW BATTERY ALARM
```

```
                MOV     R7,#0E2H            ;SET AUDIO COUNT LIMIT = -30 SEC
;
; TURN ON AUDIO PULSES FOR VARIOUS ALARM CONDITIONS
;
AUDIO           MOV     R0,#CLEARA          ;POINT TO CLEAR BIT IN PORT A
                MOV     R1,#INSTAT          ;POINT TO CURRENT ALARM STATUS
                MOV     A,@R1               ;GET CURRENT ALARM STATUS
                ANL     A,#00010110B        ;MASK IN BABY ALARMS
                JZ      LOOSE               ;IF NO BABY ALARMS ? JUMP
                MOV     R7,#0FFH            ;SET AUDIO COUNT LIMIT = -1 SEC
                MOV     R0,#SETA            ;POINT TO SET BIT IN PORT A
LOOSE           MOV     A,#00001000B        ;SET REAR PANEL ALARM STATUS BIT
                MOVX    @R0,A               ;OUTPUT REAR PANEL ALARM STATUS
                MOV     A,@R1               ;RECALL CURRENT ALARM STATUS
                ANL     A,#00100000B        ;MASK IN LEADS OFF BIT
                JZ      AUDTST              ;IF LEADS ARE ON ? JUMP
                MOV     R7,#0FEH            ;SET AUDIO COUNT LIMIT = -2 SEC
;
; OUTPUT CURRENT TIME LIMITED AUDIO PULSE
;
AUDTST          MOV     R0,#AUDCNT          ;POINT TO LSB OF AUDIO COUNTER
                MOV     A,R7                ;RECALL AUDIO LIMIT COUNT
                JZ      CLRAUD              ;IF LIMIT = 0 ? TURN OFF AUDIO
                CALL    INCSEC              ;INCREMENT AUDIO COUNTER BY 20 mSec
                MOV     A,@R0               ;RECALL MSB OF COUNTER
                DEC     R0                  ;POINT TO LSB OF AUDIO COUNTER
                JNZ     ENDAUD              ;IF MSB OF COUNTER > 0 ? JUMP
                MOV     A,@R0               ;GET LSB OF AUDIO COUNTER
                ADD     A,#0EBH             ;ADD -21 TO IT
                JC      AUDOFF              ;IF COUNT >= 20 ? JUMP
AUDON           MOV     R0,#SETA            ;POINT TO SET BIT IN PORT A
                JMP     AUDOUT              ;GOTO OUTPUT AUDIO SIGNAL
ENDAUD          ADD     A,R7                ;ADD LIMIT TO PRESENT COUNT
                JNC     AUDOFF              ;IF AUDIO COUNT < LIMIT ? JUMP
CLRAUD          CALL    CLRTWO              ;CLEAR AUDIO COUNTER
AUDOFF          MOV     R0,#CLEARA          ;POINT TO CLEAR BIT IN PORT A
AUDOUT          MOV     A,#00100000B        ;SET AUDIO INDICATOR
                MOVX    @R0,A               ;TURN ON/OFF AUDIO
;
; OUTPUT CURRENT HEART BEAT AND BREATH LEDS
;
                MOV     R0,#HRLED           ;POINT TO HEART BEAT LED COUNTER
                MOV     A,@R0               ;GET HEART BEAT LED COUNTER
                JZ      CHRLED              ;IF = 0 ? THEN JUMP AROUND
                INC     @R0                 ;INCREMENT BY 1 & SAVE AS NEW COUNT
                ORL     P1,#00000001B       ;TURN ON HEART BEAT LED
                JMP     BROUT               ;GOTO OUTPUT BREATH LED
CHRLED          ANL     P1,#11111110B       ;TURN OFF HEART BEAT LED
BROUT           INC     R0                  ;POINT TO BREATH LED COUNTER
                MOV     A,@R0               ;GET BREATH LED COUNTER
                JZ      CHRLED              ;IF COUNT = 0 ? JUMP
                INC     @R0                 ;INCREMENT BY 1 & SAVE AS NEW COUNT
                ORL     P1,#00001000B       ;TURN ON BREATH LED
                JMP     DECTST              ;GOTO OUTPUT DECAY RESPIRATION HYSTER
CBRLED          ANL     P1,#11110111B       ;TURN OFF BREATH LED
;
; INCREMENT DECAY TIMER FOR RESPIRATION HYSTERESIS
;
DECTST          MOV     R0,#DECAY           ;POINT TO DECAY TIMER
                INC     @R0                 ;INCREMENT DECAY TIMER BY 1
;
; OUTPUT CURRENT RESPIRATION BASELINE RESET STATUS
;
```

```
RBRTST    MOV     R0,#SETA        ;POINT TO SET BIT IN PORT A
          MOV     R1,#RBRCNT      ;POINT TO RESP BASELINE RESET COUNTER
          MOV     A,@R1           ;GET RBR COUNTER
          JZ      RBROUT          ;IF COUNTER = 0 ? THEN JUMP
          INC     @R1             ;ELSE INCREMENT COUNT BY 1
CLRRBR    MOV     R0,#CLEARA      ;POINT TO CLEAR BIT IN PORT A
RBROUT    MOV     A,#01000000B    ;SET RESP BASELINE RESET INDICATOR
          MOVX    @R0,A           ;OUTPUT RBR STATUS
;
; UPDATE AND OUTPUT 2 Hz SQUARE WAVE
;
SQRTST    MOV     R0,#SQUARE      ;POINT TO 2 Hz SQUARE WAVE COUNTER
          INC     @R0             ;INCREMENT BY 1
          MOV     A,@R0           ;GET SQUARE WAVE COUNTER
          ADD     A,#083H         ;ADD -125 TO IT
          JNZ     ENDINT          ;IF COUNT < 125 ? THEN JUMP AROUND
          MOV     @R0,A           ;SET COUNT = 0
          MOV     R1,#PORTA       ;POINT TO PORT A ADDRESS
          MOVX    A,@R1           ;INPUT PORT A STATUS
          XRL     A,#00010000B    ;TOGGLE 2 Hz OUTPUT
          MOVX    @R1,A           ;OUTPUT 2 Hz SQUARE WAVE
;
; RESTORE CURRENT RESPIRATION S.A.P. OUTPUT TO D/A
;
ENDINT    MOV     R0,#007H        ;POINT TO REG BANK 0 R7
          CALL    OUTDA           ;CALL ROUTINE TO OUTPUT TO D/A
;
; RESTORE STATUS AND ACCUM VALUE AND RETURN FROM INTERRUPT
;
          MOV     R0,#ACCUM       ;POINT TO TEMP ACCUM STORAGE
          MOV     A,@R0           ;RECALL STORED ACCUM
          RETR                    ;RETURN FROM INTERRUPT
;
          END
!!
```

We claim:

1. For suppressing cardiovascular artifact from a respiration signal derived from a patient, a filtering device comprising:

heat beat detecting means for detecting heart beats of the patient;

processing means for determining the heart rate of the patient in response to the detected heart beats; and filtering means operable for sampling the respiration signal in proportion to the heart rate and producing a filtered respiration signal as follows:

Filtered Respiration Signal = $S_{(t)} + (K_1+K_2)Z^{-1}_{(t-1)} + (K_3+K_4)Z^{-2}_{(t-1)}$ where:

$S_{(t)}$ is the respiration signal currently being sampled;

$Z^{-1}_{(t)} = S_{(t)} + K_1 Z^{-1}_{(t-1)} + K_3 Z^{-2}_{(t-1)}$ $Z^{-2}_{(t)} = Z^{1}_{(t-1)}$;

and $K_1$, $K_2$, $K_3$, and $K_4$ are constants.

2. A filtering device as in claim 1; wherein the heart beat detecting means comprises a QRS detecting means for detecting the QRS complex of each heart beat waveform produced by the patient.

3. A filtering device as in claim 1, wherein the processing means comprises timing means for producing pulses at a predetermined rate and first counting means for counting the number of pulses occurring between detected heart beats.

4. A filtering device as in claim 1; wherein the device further comprises conversion means for converting from an analog to a digital representation of the respiration signal at a converting rate proportional to the heart rate and wherein the filtering means samples the digital representation of the respiration signal.

5. A filtering device as in claim 4; wherein the conversion means is a successive approximating analog-to-digital converter.

* * * * *